United States Patent [19]

Terao et al.

[11] Patent Number: 4,518,602

[45] Date of Patent: May 21, 1985

[54] VINYL CARBOXYLIC ACID DERIVATIVES, THEIR PRODUCTION AND USE AS INHIBITORS OF THROMBOXANE SYNTHETASE

[75] Inventors: Shinji Terao, Toyonaka; Kohei Nishikawa, Kyoto, both of Japan

[73] Assignee: Takeda Chemical Industries, Ltd., Osaka, Japan

[21] Appl. No.: 537,862

[22] Filed: Sep. 30, 1983

[30] Foreign Application Priority Data

Oct. 7, 1982 [JP] Japan ................. 57-176918
Dec. 1, 1982 [JP] Japan ................. 57-211753

[51] Int. Cl.$^3$ ............... A61K 31/44; C07D 211/82; C07D 213/55; C07D 407/06
[52] U.S. Cl. ............... 514/332; 546/342; 546/284; 546/283; 546/267; 546/274; 546/269; 546/272; 514/336
[58] Field of Search ............... 546/342, 341, 284, 283, 546/269, 267, 274, 272; 424/263

[56] References Cited

U.S. PATENT DOCUMENTS 3,157,664  11/1964  DeWald ............... 546/342

OTHER PUBLICATIONS

Journal of Medicinal Chemistry, vol. 24, 1981, pp. 1149–1155, Highly Selective Inhibitors of Thromboxane Synthetase 2. Pyridine Derivatives, Tanouchi.
Journal of Medicinal Chemistry, vol. 24, 1981, pp. 1139–1148, Highly Selective Inhibitors of Thromboxane Synthetase, 1. Imidazole Derivatives, Iizuka.

Primary Examiner—Henry R. Jiles
Assistant Examiner—Robert C. Whittenbaugh
Attorney, Agent, or Firm—Wegner & Bretschneider

[57] ABSTRACT

Novel compound of the formula:

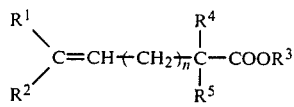

wherein $R^1$ is a pyridyl group; $R^2$ is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; $R^3$ is hydrogen, benzyl or a lower alkyl; one of $R^4$ and $R^5$ is hydrogen or a lower alkyl, and the other is an aryloxy, or lower aliphatic hydrocarbon, an alicyclic hydrocarbon having not more than 6 carbon atoms or an aromatic group which may have a substituent, or a group represented by the formula, $-S(O)_m-R^6$ (in which $R^6$ is phenyl or a lower alkyl group; m is an integer of 0 to 2), or $R^4$ and $R^5$ each combine with the other to represent one alkylene group; n is an integer of 2 to 6, or a pharmaceutically acceptable salt thereof has a selective inhibitory action on bio-synthesis of thromboxane $A_2(TXA_2)$ and an effect of enhancing the production of prostaglandin $I_2(PGI_2)$, and can be used in mammals for to prevention and treatment of arterial thrombosis caused by platelet aggregation or ischemic diseases caused by vasospasms in cardiac, cerebral and peripheral circulatory system (e.g. cardian infarction, apoplexy, infarct of blood vessels in kidney, lung and other organs, pectic ulcer, etc.).

17 Claims, No Drawings

VINYL CARBOXYLIC ACID DERIVATIVES, THEIR PRODUCTION AND USE AS INHIBITORS OF THROMBOXANE SYNTHETASE

The present invention relates to novel substituted vinylcarboxylic acid derivatives which possess the action to inhibit specifically the thromboxane $A_2(TXA_2)$ synthetase.

$TXA_2$ is a metabolite of arachidonic acid and has the platelet aggregating action. Therefore, it has been known that excessive production of $TXA_2$ in body causes various ischemic disorders in the heart, kidney and brain due to occlusion or constriction of a blood vessel. The present inventors conducted research on the synthesis of, and investigation into, materials exhibiting the inhibitory action against the $TXA_2$ synthetase, and as a result, found a group of novel compounds which possess excellent inhibitory action against the $TXA_2$ synthetase.

Thus, the present invention relates to a substituted vinylcarboxylic acid derivatives of the general formula:

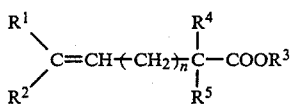

(I)

[wherein $R^1$ is a pyridyl group; $R^2$ is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; $R^3$ is hydrogen, benzyl or a lower alkyl; one of $R^4$ and $R^5$ is hydrogen or a lower alkyl, and the other is an aryloxy, or a lower aliphatic hydrocarbon, an alicyclic hydrocarbon having not more than 6 carbon atoms or an aromatic group which may have a substituent, or a group represented by the formula, $-S(O)_m-R^6$ (in which $R^6$ is phenyl or a lower alkyl group; m is an integer of 0 to 2), or $R^4$ and $R^5$ each combine with the other to represent one alkylene group; n is an integer of 2 to 6].

In the above general formula (I), as the pyridyl group represented by $R^1$ and $R^2$, there may be mentioned 2-pyridyl, 3-pyridyl and 4-pyridyl, and among these, 3-pyridyl group is preferred. With reference to the groups represented by $R^2$, the thienyl may be any of 2-thienyl and 3-thienyl, the furyl any of 2-furyl and 3-furyl, the naphthyl any of α-naphthyl and β-naphthyl, and the benzothienyl any of 2-benzothienyl, 3-benzothienyl, 4-benzothienyl, 5-benzothienyl, 6-benzothienyl and 7-benzothienyl. Referring to the substituents for the phenyl, thienyl, furyl, naphthyl, benzothienyl and pyridyl represented by $R^2$, examples of the lower alkoxy group include those of 1 to 4 carbon atoms such as methoxy, ethoxy, n-propoxy, i-propoxy, n-butoxy, i-butoxy and t-butoxy; examples of the lower alkyl group include those of 1 to 5 carbon atoms such as methyl, ethyl, n-propyl, i-propyl, n-butyl, i-butyl, t-butyl, n-pentyl and i-pentyl; examples of of the halogen atom include fluorine, chlorine and bromine; and examples of the lower alkenyl group include those of 2 to 5 carbon atoms such as vinyl, allyl and pentenyl. When the phenyl, thienyl, furyl, naphthyl, benzothienyl and pyridyl represented by $R^2$ contain substituents, such substituents can be introduced in arbitrary positions on the rings. As examples of the lower alkyl group represented by $R^3$, $R^4$ and $R^5$, there may be mentioned those of 1 to 4 carbon atoms such as methyl, ethyl, n-propyl and n-butyl. Examples of the aryloxy group represented by $R^4$ or $R^5$ include phenyloxy, 1-naphthoxy and 2-naphthoxy. As examples of the lower aliphatic hydrocarbon group, there may be mentioned those having not more than 8 carbon atoms, such as lower alkyl groups of 1 to 8 carbon atoms being exemplified by methyl, ethyl, n-propyl, n-butyl, n-pentyl, n-hexyl and n-heptyl, lower alkenyl groups of 2 to 8 carbon atoms being exemplified by vinyl, allyl, 1-methylvinyl, 3-methyl-2-butenyl, 2-pentenyl, 2-hexenyl and 2-heptenyl, and alkynyl groups of 2 to 8 carbon atoms being exemplified by ethynyl, 2-propynyl, 2-butynyl, 2-hexynyl and 2-octynyl, and among others, alkyl groups of 1 to 4 carbon atoms, alkenyl groups of 2 to 5 carbon atoms and alkynyl groups of 2 to 8 carbon atoms are preferred. As examples of the alicyclic hydrocarbon group of not more than 6 carbon atoms, there may be mentioned those having not more than 6 carbon atoms, such as cycloalkyl groups of 3 to 6 carbon atoms being exemplified by cyclopropyl, cyclobutyl, cyclopentyl and cyclohexyl, and cycloalkenyl groups of 5 to 6 carbon atoms being exemplified by cyclo-1-pentenyl and cyclo-1-hexenyl. Examples of the aromatic group represented by $R^4$ or $R^5$ include phenyl, naphthyl, 2-thienyl, 3-thienyl and 3-pyridyl. The abovementioned lower aliphatic hydrocarbon, alicyclic hydrocarbon and aromatic groups represented by $R^4$ or $R^5$ may have substituents such as hydroxyl, cyano, lower alkyl (e.g., those of 1 to 3 carbon atoms such as methyl and ethyl) and lower alkoxy groups (e.g., those of 1 to 3 carbon atoms such as methoxy and ethoxy), halogen atoms (e.g., fluorine, chlorine and bromine), phenyl and cyano-substituted phenyl groups. As examples of the group of the formula $-S(O)_mR^6$ represented by $R^4$ or $R^5$, there may be mentioned methylthio, ethylthio, isopropylthio, methylsulfinyl, ethylsulfinyl, methylsulfonyl, ethylsulfonyl, phenylthio, phenylsulfinyl, phenylsulfonyl and p-toluenesulfonyl. When $R^4$ and $R^5$ combine and cooperate together to represent one alkylene group, such alkylene group comprises 1 to 6 methylene groups being joined to one another; when $R^4$ and $R^5$ cooperate together to represent one methylene group, it signifies that the carbon to be linked by $R^4$ and $R^5$ is bonded to the methylene group through the double bond; and when $R^4$ and $R^5$ cooperate together to represent a polymethylene group of 2 to 6 carbon atoms, it denotes that there is formed a ring with the carbon to be linked by $R^4$ and $R^5$. Further, such alkylene group may have substituents in arbitrary positions. Examples of such substituent include lower alkyl groups such as methyl and ethyl, phenyl, pyridyl and thienyl groups, and these may be introduced in number of 1 to 2.

The compounds of the general formula (I) may be addition salts with pharmacologically allowable organic acids or inorganic acids, and examples of such addition salts include salts with hydrochloric acid, hydrobromic acid, phosphoric acid, sulfuric acid, citric acid, succinic acid, maleic acid, fumaric acid, methanesulfonic acid, benzenesulfonic acid, etc. In addition, when $R^3$ in the compounds (I) is a hydrogen atom, they may be alkali metal salts such as sodium and potassium salts, and alkaline-earth metal salts such as calcium salts.

Representative examples of the compounds (I) include 2,2-dimethyl-7-phenyl-7-(3-pyridyl)-6-heptenoic acid, 2.2-dimethyl-8-phenyl-8-(3-pyridyl)-7-octenoic acid, 2,2-dimethyl-7-(2-thienyl)-7-(3-pyridyl)-6-heptenoic acid, 2,2-dimethyl-8-(2-thienyl)-8-(3-pyridyl)-7-octenoic acid and 2,2-dimethyl-7-(2-naphthyl)-7-(3-pyridyl)-6-heptenoic acid.

The substituted vinylcarboxylic acid derivatives of the above general formula (I) and salts thereof have a strong inhibitory action on the thromboxane $A_2$ synthetase solubilized and fractionated from platelet microsomes of human, cows, horses, etc., and also exhibit, in mammals inclusive of human, the strong action to inhibit the biosynthesis of thromboxane $A_2(TXA_2)$ in vivo.

Furthermore, the compounds (I) of the present invention exhibit the effect of increasing the production efficiency for the dilating $I_2(PGI_2)$ that shows the arterial smooth muscle relaxation action, platelet-aggregation inhibiting action or dissociation of platelet aggregation, etc. Thus, prostaglandin $G_2(PGG_2)$ or prostaglandin $H_2(PGH_2)$ is the important intermediate for thromboxane $A_2$, prostaglandin $I_2$ and other prostaglandins, and the compounds (I) of the present invention at the very low concentrations (not greater than $3\times10^{-8}$ mole) exhibit the inhibitory action against the converting enzyme (thromboxane $A_2$ synthetase) from $PGH_2$ or $PGG_2$ to thromboxane $A_2$, whereas they show no inhibitory action against the converting enzymes to the physiologically very useful prostaglandin $I_2(PGI_2)$ and other prostaglandins, for example $PGI_2$ synthetase and prostaglandin synthetase; they rather enhance the bioavailability of $PGH_2$ and $PGG_2$, and show stimulation of $PGD_2$ production in platelets and of $PGI_2$ in the presence of vascular endothelial cells.

As is obvious from the above, the substituted vinylcarboxylic acid derivatives of the general formula (I) inhibit selectively thromboxane $A_2(TXA_2)$ synthetase, while not exhibiting the suppressive action toward prostaglandin $I_2(PGI_2)$ synthetase, prostaglandin synthetase (cyclooxygenase) and various synthetases for prostaglandins.

Also, the compounds of the present invention are extremely low in toxic effects toward rats, dogs, etc., and are characterized by a large difference between the lethal dose and the effective dose. In addition, the compounds of the present invention are less susceptible to a carbon-reduction reaction, via $\omega$-oxidation, showing long lasting action in vivo and are therefore expected to exhibit the stable $TXA_2$ synthetase inhibiting action over a long period of time. Consequently, the compounds of the present invention can reduce the amount of each dose, develop lessened side-effects even when repeatedly administered for a long period of time, and be given to mammals inclusive of human for the prophylaxis or therapy of ischemic diseases (e.g., myocardial infarction, cerebral apoplexy, infarction in the kidney, lung and so forth, ulcers in the digestive tract, etc.) due to thrombosis caused by platelet aggregation or constriction of coronary arteries, brain and peripheral and circulatory vascular systems as well as various disorders (e.g., arteriosclerosis, hypertension, etc.) caused by $TXA_2/PGI_2$ imbalance. Referring to the method of administration, they are applicable orally, for example as tablets, capsules, powders, granules, etc. and also can be administered parenterally by injections or pellets. As to the dosage, they are normally administered orally in 50 to 200 mg daily, or parenterally in 50 to 200 mg daily, being divided in one to three doses.

Among the compounds of the formula (I), a compound of the formula:

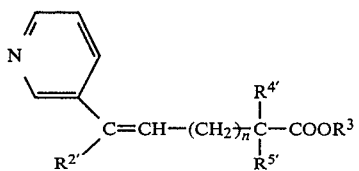

(wherein $R^{2'}$ is a phenyl or thienyl group which may optionally be substituted by a lower alkoxy, a lower alkyl, a halogen, trifluoromethyl or methylenedioxy; one of $R^{4'}$ and $R^{5'}$ is hydrogen or a lower alkyl and the other is lower alkyl or phenyl; and $R^3$ and n are as defined above) and a pharmaceutically acceptable salt thereof are preferable from the viewpoint of inhibitory action of thromboxane $A_2$ sysnthetase.

The compounds (I) of the present invention can be produced, for example, by either of the processes to be described below.

[Production process 1]

The compounds of the formula (I) can be obtained by reacting a compound of the general formula:

(wherein $R^1$, $R^2$ and n are as defined hereinbefore; X is a halogen atom) with a compound of the (III) formula:

(wherein $R^3$, $R^4$ and $R^5$ are as defined hereinbefore).

In the above general formula (II), examples of the halogen atom represented by X include bromine, iodine, etc.

This reaction is conducted normally in an anhydrous solvent under an inert gas with a strong base compound. Examples of the solvent which is useful in this reaction include dimethylsulfoxide, dimethylformamide, hexamethylenephosphortriamide, tetrahydrofuran, diethyl ether, 1,2-dimethoxyethane and solvent mixtures selected therefrom. As the inert gas, use is made of argon, helium, nitrogen, etc. The reaction temperature varies depending upon the substituents $R^4$ and $R^5$, the kind of reaction solvent and the type of strong base to be used, etc., and is normally in the range of $-70°$ C. to $30°$ C.

As the strong base compound, proper selection for utilization is made of, for example, lithium diisopropylamide, potassium hydride, sodium hydride, sodium amide, potassium tert-butoxide, lithium isopropylcyclohexylamide, etc.

The reaction normally goes to completion within 30 minutes to 3 hours.

[Production process 2]

Compounds of the formula:

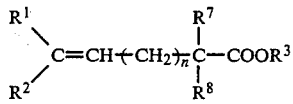  (I-2)

wherein $R^1$, $R^2$, $R^3$ and n are as defined above, and one of $R^7$ and $R^8$ is hydrogen atom or a lower alkyl group and the other is a lower aliphatic hydrocarbon group, alycyclic hydrocarbon group of not greater than 6 carbon atoms or an aromatic agroup) can be obtained by reacting a compound of the formula:

  (IV)

(wherein $R^1$ and $R^2$ are as defined hereinbefore) with a compound of the general formula:

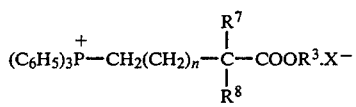  (V)

(wherein $R^3$, $R^7$, $R^8$ and n are as defined above, and $X^-$ is a halogen ion).

In the above formulas (I-2) and (V), the lower aliphatic hydrocarbon group, alicyclic hydrocarbon group of not greater than 6 carbon atoms and aromatic group represented by $R^7$ and $R^8$ are as defined by $R^4$ and $R^5$. As examples of the halogen ion represented by $X^-$, there may be mentioned chlorine, bromine and iodine ions.

This reaction is normally carried out in an organic solvent in the presence of a base. As examples of the base, there may be mentioned n-butyl lithium, lithium diisopropyl amide, sodium hydride, potassium hydride, potassium tertbutoxide and sodium amide, and among these, lithium diisopropyl amide, sodium hydride and sodium amide are preferably used. Examples of the solvent include ether, tetrahydrofuran, dimethylformamide, dimethylsulfoxide or solvent mixtures of not less than two kinds selected therefrom. This reaction is desirably conducted under an atmosphere of dry inert gas (e.g., nitrogen gas, argon gas, helium gas, etc.). The reaction temperature is −20° C. to 50° C., preferably 0° C. to 30° C. This reaction can be checked for how far the reaction proceeds by observing the disappearance of the characteristic color of phospholane, and goes to completion normally within the range of 1 to 6 hours.

[Production process 3]
Compounds of the formula:

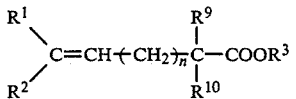  (I-3)

(wherein $R^1$, $R^2$, $R^3$ and n are as defined above, $R^9$ is hydrogen or a lower alkyl or arylthio, and $R^{10}$ is a lower aliphatic hydrocarbon group) can be produced by reacting a compound of the formula:

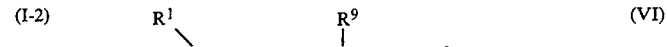  (VI)

(wherein $R^1$, $R^2$, $R^3$, $R^9$ and n are as defined hereinbefore) with a compound of the formula:

$$R^{10}-X \quad \text{(VII)}$$

(wherein $R^{10}$ and X are as defined hereinbefore).

In the above general formulae (VI) and (I-3), the lower alkyl group represented by $R^9$ is as defined for the lower alkyl group by $R^4$ or $R^5$, and examples of the arylthio group represented by $R^9$ include phenylthio and naphthylthio. In the above general formulae (VII) and (I-3), furthermore, the lower aliphatic hydrocarbon group represented by $R^{10}$ is as defined for the lower aliphatic hydrocarbon group by $R^5$.

This reaction is normally carried out in a solvent in the presence of a base. Examples of the base include n-butyl lithium, lithium diisopropylamide, lithium isopropylcyclohexylamide, sodium hydride, potassium hydride and potassium tert-butoxide. As the solvent, use is made of, for example, ether, tetrahydrofuran, dimethylsulfoxide, hexamethylphosphortriamide or solvent mixtures of not less than two kinds selected therefrom. The reaction temperature, normally, is preferably −78° C. to 0° C., and the reaction time is normally 1 to 3 hours.

[Production process 4]
Compounds of the formula:

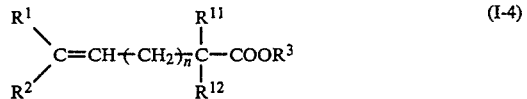  (I-4)

(wherein $R^1$, $R^2$, and $R^3$ and n are as defined above; $R^{11}$ is hydrogen or a lower alkyl; and $R^{12}$ is a lower alkyl or an aryl group) can be obtained by reacting a compound of the formula:

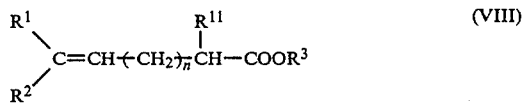  (VIII)

(wherein $R^1$, $R^2$, $R^3$, $R^{11}$ and n are defined hereinbefore) with a compound of the formula:

$$(R^{12}-S-)_2 \quad \text{(IX)}$$

(wherein $R^{12}$ is as defined above).

In the above fromulae (VIII) and (I-4), the lower alkyl group represented by $R^{11}$ is as defined for the lower alkyl group by $R^4$ or $R^5$, and examples of the lower alkyl group represented by $R^{12}$ include those of 1 to 8 carbon atoms such as methyl, ethyl, n-propyl, isopropyl, n-butyl, n-pentyl, n-hexyl, and n-heptyl.

This reaction is normally conducted in a solvent, such as tetrahydrofuran, diethyl ether and 1,2-dimethoxyethane, at the reaction temperature of −70° to 0° C., under an inert gas atmosphere and in the presence of lithium diisopropylamide or lithium isopropylcyclohexylamide, etc. The reaction time is 1 to 3 hours.

[Production process 5]
Compounds of the formula:

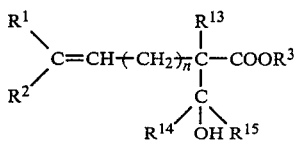 (I-5)

wherein $R^1$, $R^2$, $R^3$ and n are as defined above, $R^{13}$ is hydrogen or a lower alkyl; $R^{14}$ and $R^{15}$ each is a lower alkyl or an aryl, or combine with other to represent one alkylene group) can be obtained by reacting a compound of the formula:

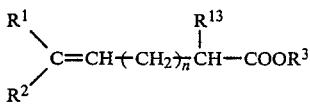 (X)

(wherein $R^1$, $R^2$, $R^3$, $R^{13}$ and n are as defined hereinbefore) with a compound of the general formula:

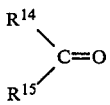 (XI)

(wherein $R^{14}$ and $R^{15}$ are as defined above).

In the above general formulae (X) and (I-5), the lower alkyl group represented by $R^{13}$ is as defined for the lower alkyl group by $R^4$ or $R^5$, and examples of the lower alkyl represented by $R^{14}$ and $R^{15}$ include those of 1 to 8 carbon atoms such as methyl, ethyl, n-propyl, n-butyl, n-pentyl, n-hexyl and n-heptyl. As the aromatic group, also, there may be mentioned phenyl and naphthyl. When $R^{14}$ and $R^{15}$ are combine with each other to represent one alkylene group, such alkylene group comprises the methylene group joined in the number of 2 to 6, whereby said alkylene group forms a ring together with the carbon atom linked by $R^4$ and $R^5$.

This reaction can be carried out under the same conditions as in the above-mentioned production process 4 in terms of the base, solvent, reaction temperature and inert gas being employed.

[Production process 6]
Compounds of the general formula:

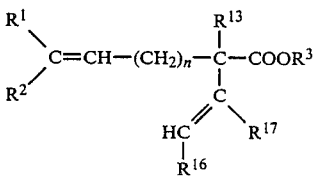 (I-6)

or of the general formula:

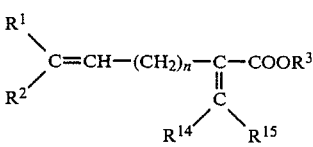 (I-7)

(wherein $R^1$, $R^2$, $R^3$, n, $R^{13}$, $R^{14}$ and $R^{15}$ are as defined hereinbefore; one of $R^{16}$ and $R^{17}$ is a hydrogen atom or a lower alkyl group, and the other is a lower alkyl group, or $R^{16}$ and $R^{17}$ combine and cooperate together to represent one alkylene group of 1 to 5 carbon atoms) can be obtained by subjecting a compound of the general formula:

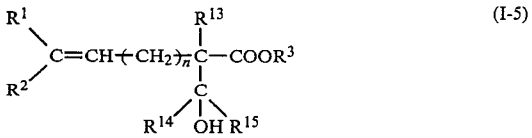 (I-5)

(wherein each of the symbols is as defined hereinbefore) to a dehydration reaction.

This reaction is carried out in an inert solvent, such as methylene chloride, chloroform, ethyl acetate, toluene, ether and tetrahydrofuran, in the presence of an organic base such as pyridine and triethylamine and with the use of a dehydrating agent such as thionyl chloride and phosphorus oxychloride.

The substituted vinylcarboxylic acid derivatives (I) as produced by the above procedures can be separated and purified by ordinary means such as extraction, concentration, crystallization and liquid chromatography. Also, the compounds (I) belong to 3-substituted olefin compounds, and in some instances, occur in two geometrical isomers. Separation of the isomers, if necessary, can be effected by fractional crystallization, chromatography or a combination thereof, etc.

When the compound of the general formula (I) is a carboxylic acid [in the formula (I), $R^3$ is a hydrogen atom], it can be derivatized into an ester form [in the formula (I), $R^3$ is a lower alkyl group] by esterification, as the case may be, and conversely, in cases where the compound (I) is an ester form, it can be derivatized into a free carboxylic acid, if necessary.

Each of compounds of the formula (I-1) has two geometrical isomers of the formulas:

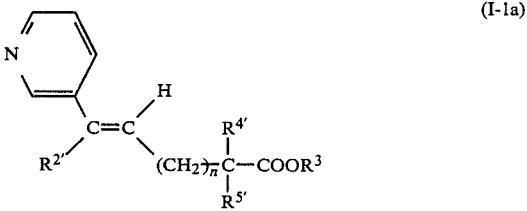 (I-1a)

and

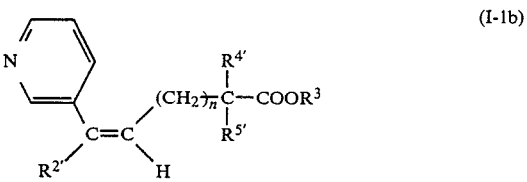 (I-1b)

wherein each symbol has the meaning given above.

In the following description of this invention, the compound wherein, as in the case of compounds represented by the formula (I-1a), the pyridine ring substituting one of the carbon atoms involved in the vinyl double bond and the hydrogen atom substituting the other carbon atom are disposed in the same direction is referred to as the E isomer and the compound wherein, as in the case of compounds represented by formula (I-1b), the pyridine ring substituting one of the carbon atoms involved in the vinyl double bond and the hydrogen atom substituting the other carbon atom are disposed in the opposite direction is referred to as the Z isomer.

The Z isomer (I-1b) can be isomerized to the E isomer (I-1a) by isomerization reaction which comprises heating the Z isomer in the presence of a mineral acid.

The isomerization reaction is generally conducted either in water or in an aqueous organic solvent. This aqueous organic solvent should basically be a solvent that is not susceptible to mineral acids. Thus, for example, mixtures of water with acetic acid, formic acid, etc. may be mentioned. The mineral acid may for example be hydrochloric acid, sulfuric acid, phosphoric acid, hydrobromic acid, perchloric acid, methanesulfonic acid or the like, although hydrochloric acid, hydrobromic acid or phosphoric acid is preferably employed. This acid is generally used in the proportion of about 6 to 15 moles per mole of the starting compound (I-1b). The reaction temperature is generally about 50° to 140° C. and preferably about 100° to 130° C. At a lower temperature, the reaction is undesirably retarded. The reaction time varies with the kind and amount of the acid catalyst used and the heating temperature. Generally, such reaction conditions are selected as would reach an equilibrium of acid isomerization in about 10 to 40 hours.

This reaction is an equilibrium reaction between E isomer (I-1a) and Z isomer (I-1b), and by subjecting either the E isomer or the Z isomer or an optional mixture of E and Z isomers to the isomerization reaction, it can be converted to a mixture consisting of about 60 to 70% of E isomer (I-1a) and about 30 to 40% of Z isomer (I-1b). Since, as aforementioned, the E isomer is pharmacologically superior to the Z isomer, this reaction is advantageously applied to mixtures containing 40% or more of Z isomer.

When this reaction is conducted using a compound of general formula (I-1b) wherein $R^3$ is a lower alkyl group as a starting material, a hydrolysis reaction takes place concurrently to give the Compound (I-1a) wherein $R^3$ is hydrogen.

The product compound (I-1a) (E isomer) obtainable by this reaction can be isolated and purified by such procedures as, for example, adjusting the reaction mixture to isoelectric point (pH 5.0 to 6.0) with aqueous ammonia, sodium hydroxide, potassium hydroxide or the like, extracting the product compound with an organic solvent such as ethyl acetate, chloroform, dichloromethane or the like and subjecting the extract to the conventional purification procedure such as crystallization or chromatography. The yield of this isomerization reaction can be improved by repetitive application thereof to the residual Z isomer-rich mixture remaining after isolation, for example by fractional crystallization, of E isomer (I-1a).

When the compounds of general formula (I-1a) and (I-1b) are carboxylic acids [In formulas (II) and (III), $R^3$ is a hydrogen atom], these acids can, if necessary, be esterified to the corresponding esters [In formulas (I-1a) and (I-1b), $R^2$ is a lower alkyl group]. Conversely, if the compounds (I-1a) and (I-1b) are esters, they can be hydrolyzed to the free carboxylic acids.

The compound (I-1) obtained in the reaction of compound (II) with compound (III) or in the reaction of compound (IV) with comound (V) is a substantially equimolar mixture of E and Z isomers. This mixture can be directly used in the practice of this invention but it is of course possible to separate the E and Z isomer from each other by way of fractional recrystallization or liquid chromatography and subjecting the Z isomer alone to the isomerization reaction mentioned above.

The compounds of the above general formula (IV) can be produced, for example as illustrated in the following manner, by reacting an organic lithium compound with an aldehyde compound to yield a compound (XIV) and then reacting said compound (XIV) with manganese dioxide or dimethylsulfoxide-oxalic chloride.

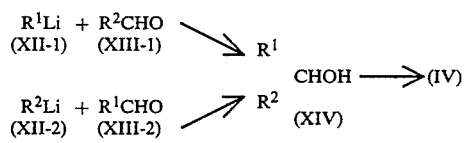

The compounds of the above general formula (II) can be produced, for example, by reducing a compound of the general formula:

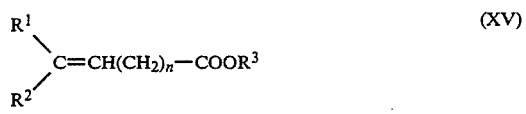

(wherein $R^1$, $R^2$, $R^3$ and n are as defined hereinbefore) with lithium aluminum hydride, etc. to convert into the corresponding alcohol form, followed by a halogenation reaction.

Also, the triphenylphosphonium salt of the above general formula (V) can be produced, for example, by the reaction to be shown below.

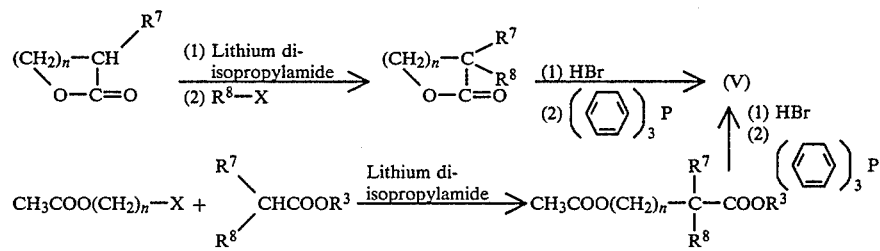

(wherein $R^3$, $R^7$, $R^8$, n and X are as defined hereinbefore).

The reference examples, examples and experiments are described below to illustrate more specifically the present invention.

With reference to the designation of isomers, the compounds in which the 3-pyridyl group and olefinic proton at the double bond substituted by the 3-pyridyl group are in the same direction are called "(E)-isomer", and the compounds in which the 3-pyridyl group and the olefin proton are in the opposite direction are called "(Z)-isomer".

In the tables to be shown in the following, the symbols denote the following groups, respectively.

3-Py: 3-pyridyl group; 2-Th, 3-Th: 2-thienyl group, 3-thienyl group; Ph: phenyl group; Me: methyl group; Et: ethyl group; PhCH$_2$: benzyl group; PhO: phenoxy group; i-Pr-S: isopropylthio; MeS-: methylthio; PhS: phenylthio. Nuclear magnetic resonance spectra were measured on an EM-390 (Varian Associates, U.S.A.) utilizing CDCl$_3$ as solvent.

REFERENCE EXAMPLE 1

Methyl (E+Z)-6-phenyl-6-(3-pyridyl)-5-hexenoate (23 g) was dissolved in anhydrous tetrahydrofuran (100 ml), and the solution was cooled with ice at 5° C. Lithium aluminum hydride (4 g) was gradually added to the solution, followed by stirring at room temperature for 3 hours. After the completion of the reaction, saturated aqueous potassium sodium tartrate was added to decompose the excessive reagent, whereby the inorganic materials were solidified. The organic layer was separated, and the remaining inorganic substance was washed with ethyl acetate. The organic layer and ethyl acetate layer were combined and concentrated under reduced pressure. The residue was chromatographed on a column of silica gel, and the elution was performed with ethyl acetate to yield (E+Z)-6-phenyl-6-(3-pyridyl)-5-hexen-1-ol (16 g). The alcohol form (15 g) was dissolved in 47% aqueous hydrobromic acid (100 ml) and the solution was heated at 100° C. for 18 hours to allow the reaction to proceed. After the cooling, the reaction solution was adjusted to pH 8 by adding sodium hydrogen-carbonate, and the resultant product was extracted with ethyl acetate. The organic layer was worked up in the usual manner, and the ethyl acetate was evaporated in vacuo. The residue was chromatographed on silica gel, using ethyl acetate:isopropyl ether (1:1) as eluant to yield (E+Z)-1-bromo-6-phenyl-6-(3-pyridyl)-5-hexene (15 g) NMR ($\delta$ value): 8.50 (2H,m), 7.30 (7H,m), 6.16 ($\frac{1}{2}$H,t,7 Hz), 6.08 ($\frac{1}{2}$H,t,7 Hz), 3.34 (2H,t,6 Hz), 2.05 (3H,m), 1.80 (3H,m)

The bromide compound (15 g) was dissolved in acetone (100 ml), and sodium iodide (25 g) was added to the solution, followed by stirring at room temperature for 1 hour. After the completion of the reaction, water (50 ml) was added, followed by extracting with ethyl acetate. The organic layer was washed with water, dried and concentrated under reduced pressure. The residue was chromatographed on silica gel using ethyl acetate:isopropyl ether (1:1) as eluant to give the Z-isomer at first and then the E isomer [(E)-1-iodo-6-phenyl-6-(3-pyridyl)-5-hexene: NMR ($\delta$ value), 8.50 (2H,m), 7.30 (7H,m), 6.08 (1H,t,7 Hz), 3.15 (2H,t,6 Hz), 2.02 (2H,m), 1.80 (2H,m); (Z)-1-iodo-6-phenyl-6-(3-pyridyl)-5-hexene: NMR ($\delta$ value), 8.50 (2H,m), 7.31 (7H,m), 6.16 (1H,t,7 Hz), 3.18 (2H,t,6 Hz), 2.00 (2H,m), 1.78 (2H,m)].

REFERENCE EXAMPLE 2

In dichloromethane (100 ml) was dissolved (E+Z)-5-phenyl-5-(3-pyridyl)-4-penten-1-ol (prepared from 3-benzoylpyridine and 4-hydroxybutyltriphenylphosphonium bromide in accordance with the Wittig reaction) [NMR ($\delta$ value): 8.34–8.60 (2H,m), 7.1–7.6 (7H,m), 6.0–6.3 (1H,m), 3.40 (2H,t), 2.0–2.4 (2H,m), 1.5–1.9 (2H,m)] (12 g), and the solution was cooled at 0° C. Triethylamine (6.0 g) was added to the solution, followed by stirring under the same conditions. A solution of methanesulfonyl chloride (6.2 g) in dichloromethane (20 ml) was added to the solution. After the completion of the reaction, water (100 ml) was added, followed by thorough shaking. The organic layer was separated, washed with water, dried and evaporated under reduced pressure to dryness. Acetone (100 ml) and sodium iodide (8 g) were added to the residue, and the reaction was allowed to proceed at room temperature for 3 hours. After the completion of the reaction, the acetone was removed under reduced pressure, and ethyl acetate (100 ml) and water (50 ml) were added to the residue to extract the products. The organic layer was washed with water, dried and freed of concentrated under reduced pressure. The residue was chromatographed on silica gel using isopropyl ether:ethyl acetate (1:1) as eluent to give the Z isomer at first and then the E isomer [(E)-1-iodo-5-phenyl-5-(3-pyridyl)-4-pentene: NMR ($\delta$ value), 8.35–8.60 (2H,m), 7.1–7.6 (7H,m), 6.07 (1H,t,7 hz), 3.42 (2H,t), 3.27 (2H,t), 2.35 (2H,m); (Z)-1-iodo-5-phenyl-5-(3-pyridyl)-4-pentene: NMR ($\delta$ value), 8.35–8.60 (2H,m), 7.1–7.6 (7H,m), 6.20 (1H,t,7 Hz), 3.43 (2H,t), 3.28 (2H,t), 2.36 (2H,m).

REFERENCE EXAMPLE 3

Production of 5-carboxy-5,5-dimethylpentyltriphenylphosphonium bromide.

(a) Ethyl 6-acetoxy-2,2-dimethylhexanoate

Diisopropylamine (8.25 ml) was dissolved in anhydrous tetrahydrofuran (100 ml) under an argon atmosphere, and the solution was cooled at −70° C. 1.6M n-butyllithium hexane solution (37 ml, 60 mmole) was added dropwise to the solution, to which a solution of ethyl isobutyrate (5.6 g, 48 mmole) in anhydrous tetrahydrofuran (5 ml) was then added, while maintaining the reaction temperature at not higher than −60° C. After stirring was continued for 30 minutes under the same reaction conditions, a solution of 4-acetoxybutyl iodide (12 g, 50 mmole) in hexamethylphosphortriamide (5 ml) was added dropwise to the reaction solution, and the reaction was allowed to proceed until the mixture rose to room temperature. After the completion of the reaction, 2N hydrochloric acid (10 ml) was added, and the mixture was concentrated under reduced pressure. The resulting product was dissolved in ethyl acetate (100 ml), and the organic layer was washed with water, dried and concentrated under reduced pressure. The residue was chromatographed on a column of silica gel using isopropyl ether to give ethyl 6-acetoxy-2,2-dimethylhexanoate (5.6 g, 50%).

(b) 6-Bromo-2,2-dimethylhexanoic acid

6-Acetoxy-2,2-dimethylhexanoic acid (4.5 g) was dissolved in 47% aqueous hydrobromic acid (25 ml), and the solution was heated at 130° C. for 4 hours. After the completion of the reaction, water (100 ml) was added to the solution, and the product was extracted with ether. The organic layer was washed with water, dried and concentrated under reduced pressure. The residue was chromatographed on a column of silica gel, and development with isopropyl ether yielded 6-bromo-2,2-dimethylhexanoic acid (4 g, 91%).

(c) 5-Carboxy-5,5-dimethylpentyltriphenylphosphonium bromide.

6-Bromo-2,2-dimethylhexanoic acid (3.8 g, 17 mmole) and triphenylphosphine (4.9 g, 18.7 mmole) were dissolved in acetonitrile (30 ml), and the solution was heated under reflux for 20 hours. After the completion of the reaction, the solvent was removed under reduced pressure, and the residue was treated with toluene, followed by thorough stirring. The insolubles were seperated from the toluene solution, and crystallized from ethyl acetate to give 5-carboxy-5,5-dimethylpentyltriphenylphosphonium bromide (4.8 g, 58%) [NMR (δ value): 1.10 (6H,s), 1.4–1.6 (6H), 3.4–3.8 (2H)].

REFERENCE EXAMPLE 4

Production of 5-carboxy-5-methylpentyltriphenylphosphonium bromide.

(a) 2-Methylcaprolactam.

1.6M n-butyllithium-hexane solution (28.9 ml, 46.2 mmole) was added dropwise to a solution of diisopropylamine (6.5 ml, 46.4 mmole) in tetrahydrofuran (50 ml) at −60° C. under an argon atmosphere, with stirring. 10 minutes later, a solution of caprolactone (5.0 g, 43.8 mmole) in tetrahydrofuran (10 ml) was added dropwise to the solution. After the reaction was allowed to proceed for 20 minutes under the same reaction conditions, a solution of methyl iodide (7.5 g, 52.8 mmole) in hexamethylphosphormaide (9.2 ml) was added gradually to the reaction solution, and stirring was continued for 1 hour after the dropwise addition while maintaining the reaction mixture at −40° to −45° C. Saturated aqueous ammonium chloride solution (20 ml) was added to the reaction solution to terminate the reaction, and water (100 ml) was added to the mixture, followed by extraction of the product with ethyl acetate. The organic layer was washed with water, dried and concentrated. The residue was chromatographed on a column of silica gel, and development with isopropyl ether yielded 2-methylcaprolactam (3.7 g, 66%) [NMR (δ value): 1.18 (3H, d, 6 Hz), 2.5–2.9 (1H,m), 4.18–4.34 (2H,m)].

(b) 6-Bromo-2-methylhexanoic acid

To 2-methylcaprolactone (1.8 g, 14 mmole) was added a solution mixture of 47% aqueous hydrobromic acid (10.5 ml) and concentrated sulfuric acid (2.6 ml), and the reaction was conducted under heating at 130° C. for 3 hours. After the reaction solution was cooled, water was added, and the product was extracted with ether. The organic layer was washed with water, dried and the solvent was evaporated in vacuo. The residue was chromatographed on a column of silica gel using isopropyl ether to give 6-bromo-2-methylhexanoic acid (1.56 g, 53.3%) [NMR (δ value): 1.18 (3H,d,6 Hz), 2.25–2.8 (1H,m), 3.40 (2H,t,6 Hz), 11.56 (1H,COOH)].

(c) 5-Carboxy-5-methylpentyltriphenylphosphonium bromide.

A solution of 6-bromo-2-methylhexanoic acid (1.08 g, 5.17 mmole) and triphenylphosphine (1.42 g, 5.4 mmole) in toluene (5 ml) was heated under reflux for 18 hours. After the solution was cooled, the crystals which separated out were collected by filtration and washed with toluene and ethyl acetate to yield 5-carboxy-5-methylpentyltriphenylphosphonium bromide (1.6 g, 64%).

REFERENCE EXAMPLE 5

Production of 5carboxy-5-phenylpentyltriphenylphosphonium bromide (a) Ethyl 6-acetoxy-2-phenylhexanoate.

Diisopropylamine (2.4 g, 23.8 mmole) was dissolved in anhydrous tetrahydrofuran (50 ml) under argon, and the solution was cooled at −70° C. 1.6M n-butyllithium-hexane solution (14.8 ml, 23.7 mmole) was added dropwise to the solution, followed by stirring at −70° C. for 10 minutes. Tetrahydrofuran (10 ml) solution containing ethyl phenylacetate (3.24 g, 20 mmole) was added, while maintaining the reaction solution at not higher than −60° C. After stirring was continued for 30 minutes under the same conditions, a solution of 4-acetoxypentyl iodide (4.8 g, 20 mmole) in hexamethylphosphortriamide (4 ml) was added dropwise to the reaction solution. Following the dropwise addition, stirring was continued at −70° C. for another 1 hour, and the reaction temperature was allowed to rise to room temperature. 2N hydrochloric acid (30 ml) was added, and the product was extracted with isopropyl ether. The organic layer was washed with water, dried and concentrated under reduced pressure. The residue was chromatographed on silica gel, and development was effected with isopropyl ether:hexane (1:1) to yield ethyl 6-acetoxy-2-phenylhexanoate (5 g, 90%).

(b) 6-Bromo-2-phenylhexanoic acid

Ethyl 6-acetoxy-2-phenylhexanoate (22 g) was dissolved in 47% aqueous hydrobromic acid (100 ml), and the solution was heated at 130° C. for 4 hours. After the completion of the reaction, the solution was cooled, and aqueous sodium chloride (300 ml) was added, followed by extraction of the product with isopropyl ether. The organic layer was washed with water, dried and concentrated under reduced pressure. The residue was chromatographed on a column of silica gel, and development was effected with isopropyl ether to give 6-bromo-2-phenylhexanoic acid (16 g, 75%).

(c) 5-Carboxy-5-phenylpentyltriphenylphosphonium bromide.

6-Bromo-2-phenylhexanoic acid (16 g, 59 mmole) and triphenylphosphine (20 g, 76 mmole) were dissolved in acetonitrile (100 ml), and the solution was heated at 100° C. for 18 hours. After the completion of the reaction, the solution was cooled and the solvent removed under reduced pressure. The residue was washed three times with toluene, whereby crystals separated out. The crystals were recrystallized from ethyl acetate to give 5-carboxy-5-phenylpentyltriphenylphosphonium bromide (21 g, 67%, m.p. 210°–215° C.).

EXAMPLE 1

(Production process 1)

Procedure A: p Diisopropylamine (0.6 g, 6 mmole) was dissolved in tetrahydrofurane (20 ml) under argon, and the solution was cooled at −70° C. 1.6M n-butyl lithium-hexane solution (4 ml) was added dropwise to the solution, and stirring was continued for 10 minutes under the same reaction conditions. A solution of methyl cyclohexanecarboxylate (0.86 g, 5.5 mmole) in tetrahydrofuran (2 ml) was added to the solution, and the mixture was stirred at −70° C. for 15 minutes. To the mixture was added dropwise a solution of (E)-6-phenyl-6-(3-pyridyl)-1-iodo-5-hexene (1.8 g, 5 mmole) in hexamethylphosphoramide (3 ml). The reaction temperature was allowed to rise gradually to room temperature, and stirring was continued for 30 minutes under the same conditions. After the completion of the reaction, water was added, and the product was extracted with ethyl acetate. The organic layer was worked up in the usual procedure, and the crude product was chromatographed on silica gel. Development was effected with isopropyl ether:ethyl acetate (2:1) to give methyl (E)-2,2-(1,5-pentamethylene)-8-phenyl-8-(3-pyridyl)-7-octenoate (1-h) (1.2 g).

Procedure B:

Methyl p-methylphenylsulfonylacetate (0.43 g, 2 mmole) was dissolved in dimethylformamide, and after the solution was cooled to 0° C. under argon, sodium hydride (0.1 g) was added, followed by stirring for 10 minutes. A solution of (Z)-6-phenyl-6-(3-pyridyl)-1-iodo-5-hexene (0.8 g) in dimethylformamide (4 ml) was added to the reaction solution, and the reaction was carried out at room temperature for 3 hours. After the completion of the reaction, water (30 ml) was added, and the product was extracted with ethyl acetate. Working up in the usual procedure, the resulting product was chromatographed on silica gel, and development was effected with isopropyl ether:ethyl acetate (1:1) to yield methyl (Z)-8-phenyl-8-(3-pyridyl)-2-(p-methylphenylsulfonyl)-7-octenoate (1-c) (0.6 g, 61%).

Procedure C:

Methyl (E)-2,2-(1,5-pentamethylene)-8-phenyl-8-(3-pyridyl)-7-octenoate (1-h) (0.2 g) was dissolved in aqueous methanol (40 ml), and lithium hydroxide (0.3 g) was added, followed by heating under reflux for 48 hours. After the completion of the reaction, the solvent was removed under reduced pressure, and the residue was adjusted to pH 6 with 2N hydrochloric acid. The product was extracted with ethyl acetate, and the extract was washed with water, dried and concentrated under reduced pressure. The residue was chromatographed on silica gel, and development was effected with ethyl acetate, whereby there was obtained (E)-2,2-(1,5-pentamethylene)-8-phenyl-8-(3-pyridyl)-7-octenoic acid (1-f) (0.18 g) from the eluate resulting after the first effluent was discarded.

By following the procedures as described in the above example, there were produced the compounds (1-a through 1-u) shown in Table I.

TABLE I

| Compound | $R^1$ | $R^2$ | $R^3$ | $R^4$ | $R^5$ | n | Isomer | Analogous example | Formula melting point | NMR Spectrum (δ value p.p.m., TMS internal standard) |
|---|---|---|---|---|---|---|---|---|---|---|
| 1-a | 3-Py | Ph | H | OPh | H | 4 | Z | A | $C_{25}H_{25}NO_3$ | 1.52(6H,m),2.00(2H,m),4.58(1H,t,7Hz),6.15(1H,t,7Hz)7.16(12H,m),8.50(2H,m),10.6(1H,COOH) |
| 1-b | 3-Py | Ph | H | $-SO_2-\text{C}_6\text{H}_4-CH_3$ | H | 4 | Z | C | $C_{26}H_{27}NO_4S$ | 1.57(4H,m),2.14(2H,m),2.37(3H,s),3.94(1H,m),6.11(1H,t,7Hz),7.31(9H,m),7.76(2H,d,8Hz),8.39(1H,m),8.64(1H,m),10.80(1H,COOH) |
| 1-c | 3-Py | Ph | Me | $-SO_2-\text{C}_6\text{H}_4-CH_3$ | H | 4 | Z | B | $C_{27}H_{29}NO_4S$ | 1.35(4H,m),2.02(4H,m),2.43(3H,s),3.66(3H,s),3.87(1H,m),6.08(1H,t,7Hz),7.21(9H,m),7.67(2H,d,9Hz),8.39(1H,d,2Hz),8.53(1H,dd,2Hz,4Hz) |
| 1-d | 3-Py | Ph | H | $-SO_2-\text{C}_6\text{H}_4-CH_3$ | H | 4 | E | C | $C_{26}H_{27}NO_4S$ | 1.40(4H,m),2.00(4H,m),2.37(3H,s),3.89(1H,t,7Hz),6.11(1H,t,7Hz),7.19(9H,m),7.42(2H,d,8Hz),8.35(1H,m),8.48(1H,m),10.4(1H,COOH) |
| 1-e | 3-Py | Ph | H | $-SO-\text{C}_6\text{H}_5$ | H | 3 | (E + Z) | B | $C_{24}H_{23}NO_3S$ | 1.62(4H,m),2.08(2H,m),3.64(1H,m),6.05(1H,m),7.42(12H,m),11.40(1H,COOH) |
| 1-f | 3-Py | Ph | H | $-(CH_2)_5-$ |  | 4 | E | A,C | $C_{24}H_{29}NO_2$ | 1.37(14H,m),2.09(4H,m),6.08(1H,t,7Hz),7.15(7H,m),8.42(1H,dd,2Hz,4Hz),8.48(1H,d,2Hz),9.10(1H,COOH) |
| 1-g | 3-Py | Ph | H | $-(CH_2)_5-$ |  | 4 | Z | A,C | $C_{24}H_{29}NO_2$ 123–124° C. | 1.36(14H,m),2.02(4H,m),6.13(1H,t,7Hz),7.19(6H,m),7.49(1H,dt,2Hz,7Hz),7.98(1H,COOH),8.43(2H,d,2Hz),8.51(2H,dd,2Hz,4Hz) |
| 1-h | 3-Py | Ph | Me | $-(CH_2)_5-$ |  | 4 | E | A | $C_{25}H_{31}NO_2$ | 1.34(14H,m),2.08(4H,m),3.62(3H,s),6.06(1H,t,7Hz),7.22(7H,m),8.42(1H,dd,2Hz,4Hz)8.49(1H,d,2Hz) |
| 1-i | 3-Py | Ph | Me | $-(CH_2)_5-$ |  | 4 | Z | A | $C_{25}H_{31}NO_2$ | 1.32(14H,m),2.05(4H,m),3.62(3H,s),6.12(1H,t,7Hz),7.21(6H,m),7.43(1H,dt,2Hz,7Hz)8.44(1H,d,2Hz),8.51(1H,dd,2Hz,4Hz) |
| 1-j | 3-Py | Ph | Me | $-SO_2-\text{C}_6\text{H}_4-CH_3$ | H | 4 | Z | B | $C_{27}H_{29}NO_4S$ | 1.50(2H,m),2.09(4H,m),2.43(3H,s),3.65(3H,s),3.86(1H,m),5.97(1H,t,7Hz),7.33(9H,m),7.68(2H,d,8Hz),8.45(2H,m) |

TABLE I-continued

| Compound | R¹ | R² | R³ | R⁴ | R⁵ | n | Isomer | Analogous example | Formula melting point | NMR Spectrum (δ value p.p.m., TMS internal standard) |
|---|---|---|---|---|---|---|---|---|---|---|
| 1-k | 3-Py | Ph | Me | —SO—C₆H₅ | H | 3 | (E + Z) | B | C₂₅H₂₃NO₃S | 1.60(4H,m),2.10(4H,m),3.40 (1H,m),3.5–3.55(3H),6.05(1 H,m),7.33(7H,m),7.50(5H,s) 8.50(2H,m) |
| 1-l | 3-Py | Ph | H | Me | Me | 4 | E | A,C | C₂₁H₂₅NO₂ | 1.18(6H,s),1.42(6H,m),2.12 (2H,m),6.11(1H,t,7Hz),7.20 (6H,m),7.45(1H,dt,2Hz,7Hz) 8.54(2H,m),11.1(1H,COOH) |
| 1-m | 3-Py | Ph | H | Me | Me | 4 | Z | A,C | C₂₁H₂₅NO₂ 109–110° C. | 1.16(6H,s),1.40(6H,m),2.10 (2H,m),6.14(1H,t,7Hz),7.18 (6H,m),7.51(1H,dt,2Hz,7Hz) 8.51(2H,m),11.2(1H,COOH) |
| 1-n | 3-Py | Ph | H | Ph | H | 4 | E | A,C | C₂₅H₂₅NO₂ | 1.38(4H,m),2.08(2H,m),3.51 (1H,t),6.05(1H,t,7Hz),7.27 (6H,m),7.42(1H,dt,7Hz,2 Hz),8.41(1H,dd,2Hz,7Hz), 8.48(1H,d,2Hz) |
| 1-o | 3-Py | Ph | H | Ph | H | 4 | Z | A,C | C₂₅H₂₅NO₂ 119–120° C. | 1.36(6H,m),2.02(2H,m),3.50 (1H,t),6.09(1H,t,7Hz),7.27 (6H,m),7.45(1H,d,7Hz),8.40 (1H,m),8.50(1H,m) |
| 1-p | 3-Py | Ph | H | Et | Me | 4 | E | C | C₂₂H₂₇NO₂ | 0.84(3H,t,7Hz),1.09(3H,s), 1.39(8H,m),2.11(2H,m),6.10 (1H,t,7Hz),7.20(6H,m),8.43 (2H,dt,2Hz,7Hz),8.43(1H, dd,2Hz,4Hz),8.53(1H,d,2Hz) 10.8(1H,COOH) |
| 1-q | 3-Py | Ph | H | Et | Me | 4 | Z | C | C₂₂H₂₇NO₂ | 0.83(3H,t,7Hz),1.09(3H,s), 1.39(8H,m),2.05(2H,m),6.14 (1H,t,7Hz),7.19(6H,m),7.51 (1H,d,7Hz),8.45(2H,m), 9.31(1H,COOH) |
| 1-r | 3-Py | Ph | Et | Me | Me | 4 | E | A | C₂₃H₂₉NO₂ | 1.12(6H,s),1.19(3H,t,7Hz), 1.39(6H,m),2.17(2H,m),2.07 (2H,q,7Hz),6.10(1H,t,7Hz), 7.35(7H,m),8.50(2H,m) |
| 1-s | 3-Py | Ph | Et | Me | Me | 4 | Z | A | C₂₃H₂₉NO₂ | 1.12(6H,s),1.19(3H,t,7Hz), 1.39(6H,m),2.13(2H,m),4.07 (2H,q,7Hz),6.14(1H,t,7Hz), 7.20(6H,m),7.50(1H,m),8.50 (2H,m) |
| 1-t | 3-Py | Ph | Et | Ph | H | 4 | E | A | C₂₇H₂₉NO₂ | 1.16(3H,t,7Hz),1.50(4H,m), 2.06(2H,m),3.46(1H,t,7Hz), 4.08(2H,q,7Hz),6.03(1H,t, 7Hz),7.22(7H,m),7.25(5H,s), 8.45(2H,m) |
| 1-u | 3-Py | Ph | Et | Ph | H | 4 | Z | A | C₂₇H₂₉NO₂ | 1.16(3H,t,7Hz),1.40(4H,m), 2.03(2H,m),3.46(1H,t,7Hz), 4.08(2H,q,7Hz),6.09(1H,t, 7Hz),7.20(6H,m),7.26(5H,s), 7.42(1H,dt,2Hz,7Hz),8.41 (1H,d,2Hz),8.52)1H,dd,2 Hz,4Hz) |

EXAMPLE 2

(Production Process 2)

Procedure A:

Sodium hydride (2.5 g, 60% oil dispersion) was washed with hexane, to make clean of the oil and dried under reduced pressure. Dimethylsulfoxide (25 ml) was added to it, and the mixture was heated under argon at 80° C. for 1 hour to produce dimsyl anions. The reaction solution was cooled at 10° C., and 5-carboxy-5,5-dimethylpentyltriphenylphosphonium bromide (8 g, 16 mmole) was added, followed by stirring at room temperature for another 10 minutes. A dimethylsulfoxide solution (5 ml) containing 3-benzoylpyridine (3 g, 16 mmole) was added dropwise to the mixture solution, and after the completion of the dropwise addition, stirring was continued at room temperature for 30 minutes. Water (50 ml) was added to the mixture, which was then shaken. The organic layer was separated, and the water layer was adjusted to pH 6.0 with 2N hydrochloric acid. The product was extracted three times with ethyl acetate (50 ml). The ethyl acetate layers were combined, washed with water, dried (over magnesium sulfate) and concentrated under reduced pressure. The residue was chromatographed on a column of silica gel, and development was effected with ethyl acetate to yield (E)+(Z)-2,2-dimethyl-7-phenyl-7-(3-pyridyl)-6-heptenoic acid (2-a, 2-b) (2.2. g).

Procedure B:

5-Carboxy-5,5-dimethylpentyltriphenylphosphonium bromide (3 g, 6 mmole) was dissolved in anhydrous dimethylsulfoxide (30 ml) under a nitrogen atmosphere, and sodium hydride (0.25 g, 64 mmole) was added to the solution at 30° to 35° C., followed by stirring at 25° to 30° C. for 30 minutes. 3-Benzoylpyridine (0.9 g, 5 mmole) was added to the solution, followed by stirring at room temperature for another 1 hour. Water (100 ml) and toluene (100 ml) were added to the reaction solution, the organic layer was separated, and the water layer was adjusted to pH 6.0 with 2N hydrochloric acid. The product was extracted with ethyl acetate, and the ethyl acetate layer was washed with water, dried and concentrated under reduced pressure. The residue was chromatographed on a column of silica gel, and development was effected with ethyl acetate to yield (E+Z)-2,2-dimethyl-7-phenyl-7-(3-pyridyl)-6-heptenoic acid (2-a, 2-b) (1.36 g, 88%).

Method 1:

(E+Z)-2,2-dimethyl-7-phenyl-7-(3-pyridyl)-6-heptenoic acid (622 mg, 2 mmole) was dissolved in hexamethylphosphotriamide (10 ml), and potassium hydroxide (120 mg) and benzyl bromide (350 mg) were added to the solution, followed by stirring at room temperature. After the completion of the reaction, water (50 ml) was added to the reaction solution, and the product was extracted with ethyl acetate. The organic layer was washed with water, dried and concentrated under reduced pressure. The residue was chromatographed on silica gel, and development with ethyl acetate:isopropyl ether (1:1) gave benzyl (Z)-2,2-dimethyl-7-phenyl-(3-pyridyl)-6-heptenoate (2-g) (262 mg) at first, and then benzyl (E)-2,2-dimethyl-7-phenyl-7-(3-pyridyl)-6-heptenoate (2-f) (282 mg).

Method 2

(E+Z)-2-phenyl-7-(3-pyridyl)-7-(2-thienyl)-6-heptenoic acid (660 mg) was dissolved in ethanol (10 ml), and thionyl chloride (450 mg) was added to the solution under ice-cooling, followed by allowing the mixture to stand at room temperature for 5 hours. The reaction solution was concentrated under reduced pressure, and the residue was treated with water. The mixture was neutralized by adding sodium carbonate, and the product was extracted with ethyl acetate. The organic layer was washed with water, dried and concentrated. The residue was chromatographed on silica gel, and development was effected with acetic acid:isopropyl ether (2:1) to yield at first ethyl (Z)-2-phenyl-7-(3-pyridyl)-7-(2-thienyl)-6-heptenoate (2-i)(220 mg) and then ethyl (E)-2-phenyl-7-(3-pyridyl)-7-(2-thienyl)-6-heptenoate (2-h)(235 mg).

By following the procedures as described in the above Procedures A and B and Methods 1 and 2, there were produced the compounds (2-a through 2-n) to be shown in Table II.

TABLE II

| Compound | $R^1$ | $R^2$ | $R^3$ | $R^4$ | $R^5$ | n | Isomer | Analogous example |
|---|---|---|---|---|---|---|---|---|
| 2-a | 3-Py | Ph | H | Me | Me | 3 | E | A,B |
| 2-b | 3-Py | Ph | H | Me | Me | 3 | Z | A,B |
| 2-c | 3-Py | 2-Th | H | Me | Me | 3 | E | A,B |
| 2-d | 3-Py | 2-Th | H | Me | Me | 3 | Z | A,B |
| 2-e | 3-Py | 3-Th | H | Me | H | 3 | (E + Z) | A |
| 2-f | 3-Py | Ph | CH$_2$Ph | Me | Me | 3 | E | A + 1 |
| 2-g | 3-Py | Ph | CH$_2$Ph | Me | Me | 3 | Z | A + 1 |
| 2-h | 3-Py | 2-Th | Et | Ph | H | 3 | E | A + 2 |
| 2-i | 3-Py | 2-Th | Et | Ph | H | 3 | Z | A + 2 |
| 2-j | 3-Py | Ph | Et | Ph | H | 3 | E | A + 2 |
| 2-k | 3-Py | Ph | Et | Ph | H | 3 | Z | A + 2 |
| 2-l | 3-Py | Ph | H | Ph | H | 3 | E | A |
| 2-m | 3-Py | Ph | H | Ph | H | 3 | Z | A |
| 2-n | 3-Py | 2-Th | H | Ph | H | 3 | E | A |

| Compound | Formula | melting point | NMR Spectrum (δ value, p.p.m., TMS internal standard) |
|---|---|---|---|
| 2-a | $C_{20}H_{23}NO_2$ | | 1.18(6H, s), 1.50(4H, m), 2.12 (2H, m), 6.12(1H, t,7Hz), 7.20 (6H, m), 7.40(1H, dt, 2Hz, 7Hz), 8.44(1H, dd, 2Hz, 4Hz), 8.56 (2H, d, 2Hz), 9.82(1H, COOH) |
| 2-b | $C_{20}H_{23}NO_2$ | 137–138° C. | 1.18(6H, s), 1.51(4H, m), 2.05 (2H, m), 6.16(1H, t, 7Hz), 7.20 (6H, m), 7.50(1H, dt, 6Hz, 2 Hz), 8.46(1H, d, 2Hz), 8.55(1 H, dd, 6Hz, 2Hz), 9.70(1H, COOH) |
| 2-c | $C_{18}H_{21}NO_2S$ | | 1.19(3H, s), 1.21(3H, s), 1.52 (4H, m), 2.04(2H, m), 6.06(1H, t, 7Hz), 6.66(1H, m), 7.30(4H, m), 8.56(2H, m), 12.0(1H, COOH) |
| 2-d | $C_{18}H_{21}NO_2S$ | | 1.19(3H, s), 1.21(3H, s), 1.52 (4H, m), 2.03(2H, m), 6.21(1H, t, 7Hz), 6.66(1H, m), 7.30(4H, m), 8.56(2H, m), 12.0(1H, COOH) |
| 2-e | $C_{17}H_{19}NO_2S$ | | 1.10(3H, d, J = 3.6 Hz), 1.18(3 H, d, J = 3.6 Hz), 1.35–1.70(4H), 1.90–2.55(3H), 6.03(1H, t, J = 6.0 Hz), 6.20(1H, t, J = 6.0 Hz), 6.46(1H), 6.75–7.70(4H), 8.45–8.70(2H), 11.00(1H) |
| 2-f | $C_{27}H_{29}NO_2$ | | 1.17(6H, s), 1.46(4H, m), 2.09 (2H, m), 5.07(2H, s), 6.00(1H, t, 7 Hz), 7.20(7H,m), 7.29(5H, s), 8.45(2H, m) |
| 2-g | $C_{27}H_{29}NO_2$ | | 1.17(6H, s), 1.45(4H, m), 2.07 (2H, m), 5.08(2H, s), 6.06(1H, t, 7Hz), 7.20(6H, m), 7.30(5H, s), 7.41(1H, dt, 2Hz, 7Hz), 8.41(1H, d, 2Hz), 8.52(1H, dd, 2Hz, 4Hz) |
| 2-h | $C_{24}H_{25}NO_2S$ | | 1.22(3H, t, 7Hz), 180(4H, m 2.37(2H, m), 3.51(1H, t, 7Hz), 4.08(2H, q, 7Hz), 5.95(1H, t, 7Hz), 6.78(1H, m), 7.10(3H, m), 7.30(5H, s), 7.51(1H, dt, 2Hz 7Hz), 8.45(1H, dd, 2Hz, 4Hz), 8.53(1H, d, 7Hz) |
| 2-i | $C_{24}H_{25}NO_2S$ | | 1.15(3H, t, 7Hz), 1.40(4H, m), 2.05(2H, m), 3.41(1H, t, 7Hz), 4.06(2H, q, 7Hz), 6.14(1H, t, 7Hz), 6.46(1H, d, 3Hz), 6.81 (1H, m), 7.10(2H, m), 7.23(5H, s), 7.50(1H, d, t, 2Hz, 7Hz), 8.43(1H, d, 2Hz), 8.56(1H, dd, 2Hz, 4Hz) |
| 2-j | $C_{26}H_{27}NO_2$ | | 1.22(3H, t, 7Hz), 1.82(4H, m), 2.43(2H, m), 3.51(1H, t, 7Hz), 4.09(2H, q, 7Hz), 6.01(1H, t, 7Hz), 7.2–7.3(12H, m), 7.40(1 H, dt, 2Hz, 7Hz), 8.44(1H, dd, 2Hz, 4Hz), 8.56(2H, d, 2Hz) |
| 2-k | $C_{26}H_{27}NO_2$ | | 1.23(3H, t, 7Hz), 1.83(4H, m), 2.44(2H, m), 3.50(1H, t, 7Hz), 4.10(2H, q, 7Hz), 6.11(1H, t, 7Hz), 7.2–7.3(12H, m), 7.40(1 H, dt, 2Hz, 7Hz), 8.44(1H, dd, 2Hz, 4Hz), 8.56(2H, d, 2Hz) |
| 2-l | $C_{24}H_{23}NO_2$ | | 1.80(4H, m), 2.37(2H, m), 3.51 (1H, t, 7Hz), 6.01(1H, t, 7Hz), 7.20(6H, m), 7.40(1H, dt, 2Hz, 7Hz), 8.44(1H, dd, 2Hz, 4Hz), 8.56(2H, d, 2Hz), 9.88(1H, COOH) |
| 2-m | $C_{24}H_{23}NO_2$ | | 1.43(4H, m), 2.10(2H, m), 3.41 (1H, t, 7Hz), 6.16(1H, t, 7Hz), 7.20(6H, m), 7.50(1H, dt, 6Hz, 2Hz), 8.46(1H, d, 2Hz), 8.55 (1H, dd, 6Hz, 2Hz), 9.78(1H, COOH) |
| 2-n | $C_{22}H_{21}NO_2S$ | | 1.52(4H, m), 2.23(2H, m), 3.50 (1H, t, 7Hz), 6.10(1H, t, 7Hz), 7.30(4H, m), 8.56(2H, m), 1.17 (1H, COOH) |

EXAMPLE 3-1

(Production Process 3)

A solution of diisopropylamine (0.21 ml, 1.46 mmole) in tetrahydrofurane (3 ml) was cooled at −60° C. under argon, and a hexane solution of n-butyl lithium (1.6M, 0.92 ml, 1.46 mmole) was added dropwise to the solution. After stirring for 10 minutes, a solution of methyl (E)-7-phenyl-7-(3-pyridyl)-6-heptenoate (360 mg, 1.22 mmole) in tetrahydrofuran (2 ml) was added dropwise to the solution, followed by stirring at −60° to −70° C. for 20 minutes. Subsequently, methyl iodide (0.12 ml, 1.83 mmole) was added, and the reaction was allowed to proceed at the same temperature for 1 hour. Saturated aqueous ammonium chloride was added to the reaction mixture, and the product was extracted with ethyl acetate. The organic layer was washed with water, dried (magnesium sulfate) and concentrated. The residue was chromatographed on silica gel, and development was effected with isopropyl ether:ethyl acetate (7:3) to yield methyl (E)-2-methyl-7-phenyl-7-(3-pyridyl)-6-heptenoate (3-a) (270 mg, 71.6 %).

The compounds (3-a through 3-p) as shown in Table III-1 were produced in accordance with the above procedure.

TABLE III-1

| Compound | $R^1$ | $R^2$ | $R^3$ | $R^4$ | $R^5$ | n | Isomer | Formula | NMR Spectrum ($\delta$ value, p.p.m., TMS internal standard) |
|---|---|---|---|---|---|---|---|---|---|
| 3-a | 3-Py | Ph | Me | Me | H | 3 | E | $C_{20}H_{23}NO_2$ | 1.07(3H,s),1.20–1.70(4H,m), 2.0–2.5(3H,m),3.63(3H),6.07 (1H), 7.0–7.5(7H),8.35–8.65 (2H) |
| 3-b | 3-Py | Ph | Me | Me | H | 3 | Z | $C_{20}H_{23}NO_2$ | 1.13(3H,s),1.2–1.7(4H,m), 2.0–2.5(3H),3.63(3H),6.13(1 H),7.0–7.5(7H),8.35–8.65(2H) |
| 3-c | 3-Py | Ph | Me | Et | H | 3 | E | $C_{21}H_{25}NO_2$ | 0.87(3H),1.30–1.70(6H),2.00– 2.30(3H),3.63(3H),6.07(1H), 7.00–7.50(7H),8.40(1H),8.48 (1H) |
| 3-d | 3-Py | Ph | Me | $PhCH_2$ | H | 3 | E | $C_{26}H_{27}NO_2$ | 1.30–1.70(4H),2.00–2.30(2H), 2.50–3.50(3H),3.57(3H),6.03 (1H),7.00–7.50(7H),8.43(1H), 8.47(1H) |
| 3-e | 3-Py | Ph | Me | $PhCH_2$ | H | 3 | Z | $C_{26}H_{27}NO_2$ | 1.30–1.70(4H),1.90–2.30(2H), 2.50–3.50(3H),3.57(3H),6.07 (1H),7.00–7.50(7H),8.42(1H), 8.53(1H) |
| 3-f | 3-Py | Ph | Me | $CH_2{=}CH{-}CH_2{-}$ | H | 3 | E | $C_{22}H_{25}NO_2$ | 1.25–1.65(4H),2.00–2.45(5H), 3.63(3H),4.93(1H),5.07(1H), 5.40–5.90(1H9,6.07(1H),7.00– 7.50(7H),8.42(1H),8.48(1H) |
| 3-g | 3-Py | Ph | Me | $CH_2{=}CH{-}CH_2{-}$ | H | 3 | Z | $C_{22}H_{25}NO_2$ | 1.20–1.70(4H),1.80–2.50(5H), 3.63(3H),4.90(1H),5.07(1H), 5.40–6.00(1H),6.12(1H),7.00– 7.50(7H),8.43(1H),8.53(1H) |
| 3-h | 3-Py | Ph | Me | $HC{\equiv}C{-}CH_2{-}$ | H | 3 | E | $C_{22}H_{23}NO_2$ | 1.20–1.85(4H),1.97(1H),2.00– 2.65(5H),3.67(3H),6.07(1H), 7.00–7.50(7H),8.40(1H),8.50 (1H) |
| 3-i | 3-Py | Ph | Me | $CH_2OCH_3$ | H | 3 | E | $C_{21}H_{25}NO_3$ | 1.20–1.70(4H),2.00–2.90(3H), 3.27(3H),3.40–3.70(2H),3.63 (3H),6.07(1H),7.00–7.50(7H), 8.40(1H),8.50(1H) |
| 3-j | 3-Py | 2-Th | Me | $CH_2{=}CH{-}CH_2{-}$ | H | 3 | E + Z | $C_{20}H_{23}NO_2S$ | 1.30–1.70(4H),1.90–2.60(5H), 3.63(3H),4.90–5.30(2H),5.50– 7.70(7H),8.47(1H),8.57(1H) |
| 3-k | 3-Py | Ph | Me | 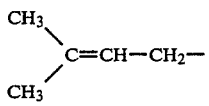 | H | 3 | E | $C_{24}H_{29}NO_2$ | 1.30–1.50(4H),1.57(3H),1.67 (3H),1.95–2.50(5H),3.63(3H), 5.00(1H),6.07(1H),7.00–7.55 (7H), 8.43(1H),8.48(1H) |
| 3-l | 3-Py | Ph | Me | $CH_3(CH_2)_2C{\equiv}C{-}CH_2{-}$ | H | 3 | E | $C_{25}H_{29}NO_2$ | 0.90(3H),1.20–1.80(6H),1.95– 2.60(7H),3.67(3H),6.07(1H), 7.00–7.50(7H),8.40(1H),8.48 (1H) |
| 3-m | 3-Py | Ph | Me | $CH_3(CH_2)_4C{\equiv}C{-}CH_2{-}$ | H | 3 | E | $C_{27}H_{33}NO_2$ | 0.87(3H),1.20–1.80(10H),2.00– 2.60(7H),3.67(3H),6.07(1H), 7.00–7.50(7H),8.40(1H),8.48 (1H) |
| 3-n | 3-Py | Ph | Me | 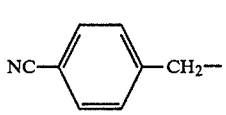 | H | 3 | E | $C_{27}H_{26}N_2O_2$ | 1.50(4H,m),2.09(2H,m),2.80 (3H,m), 3.54(3H,s),6.03(1H t,7Hz),7.32(9H,m),7.52(2H, d,8Hz),8.43(1H,m),8.48(1H, m) |
| 3-o | 3-Py | 2-Th | Et | Me | Me | 3 | E | $C_{20}H_{25}NO_2S$ | 1.13(6H,s),1.28(3H,t,7Hz), 1.38(4H,m),2.02(2H,m),4.07 (2H,q,7Hz),6.09(1H,t,7Hz), 6.48(1H,d,3Hz),6.83(1H,dd, |

TABLE III-1-continued

| Compound | R¹ | R² | R³ | R⁴ | R⁵ | n | Isomer | Formula | NMR Spectrum (δ value, p.p.m., TMS internal standard) |
|---|---|---|---|---|---|---|---|---|---|
| | | | | | | | | | 4Hz,3Hz),7.12(1H,d,4Hz), 7.32(1H,dd,4Hz,7Hz),7.56 (1H,dt,2Hz,7Hz),8.48(1H, d,2Hz),8.58(1H,dd,2Hz) |
| 3-p | 3-Py | 2-Th | Et | Me | Me | 3 | Z | $C_{20}H_{25}NO_2S$ | 1.12(6H,s),1.27(3H,t,7Hz), 1.38(4H,m),2.01(2H,m),4.07 (2H,q,7Hz),6.18(1H,t,7Hz), 6.49(1H,d,3Hz),6.83(1H,dd, 4Hz,3Hz),7.11(1H,d,4Hz), 7.30(1H,dd,4Hz,7Hz),7.56 (1H,dt,2Hz,7Hz),8.48(1H, d,2Hz),8.58(1H,dd,2Hz) |

EXAMPLE 3-2

Methyl (E)-2-methyl-7-phenyl-7-(3-pyridyl)-6-heptenoate (270 mg, 0.87 mmole) was dissolved in methanol (2 ml), and sodium hydroxide (300 mg) and water (1 ml) were added to the solution, followed by allowing the reaction to proceed at 80° C. for 2 hours. After the reaction solution was cooled, water and then 2N hydrochloric acid were added to adjust to pH 5.0, and the product was extracted with ethyl acetate. The organic layer was washed with water, dried (magnesium sulfate) and concentrated. The residue was chromatographed on silica gel, and development was effected with ethyl acetate to yield (E)-2-methyl-7-phenyl-(3-pyridyl)-6-heplenoic acid (3'-a) (217 mg, 84%).

The compounds (3'-a through 3'-q) as shown in Table III-2 were produced in accordance with the above procedure.

TABLE III-2

| Compound | R¹ | R² | R³ | R⁴ | R⁵ | n | Isomer |
|---|---|---|---|---|---|---|---|
| 3'-a | 3-Py | Ph | H | Me | H | 3 | E |
| 3'-b | 3-Py | Ph | H | Me | H | 3 | Z |
| 3'-c | 3-Py | Ph | H | Et | H | 3 | E |
| 3'-d | 3-Py | Ph | H | PhCH₂ | H | 3 | E |
| 3'-e | 3-Py | Ph | H | PhCH₂ | H | 3 | Z |
| 3'-f | 3-Py | Ph | H | CH₂=CH—CH₂— | H | 3 | E |
| 3'-g | 3-Py | Ph | H | CH₂=CH—CH₂— | H | 3 | Z |
| 3'-h | 3-Py | Ph | H | HC≡C—CH₂— | H | 3 | E |
| 3'-i | 3-Py | Ph | H | CH₂OCH₃ | H | 3 | E |
| 3'-j | 3-Py | 2-Th | H | CH₂=CH—CH₂— | H | 3 | E + Z |
| 3'-k | 3-Py | Ph | H | (CH₃)₂C=CH—CH₂— | H | 3 | E |
| 3'-l | 3-Py | Ph | H | CH₃(CH₂)₂C≡C—CH₂— | H | 3 | E |
| 3'-m | 3-Py | Ph | H | CH₃(CH₂)₄C≡C—CH₂— | H | 3 | E |
| 3'-n | 3-Py | Ph | H | NC—C₆H₄—CH₂— | H | 3 | E |
| 3'-o | 3-Py | 2-Th | H | Me | Me | 3 | E |
| 3'-p | 3-Py | 2-Th | H | Me | Me | 3 | Z |
| 3'-q | 3-Py | 2-Th | H | Et | H | 3 | (E + Z) |

| Compound | Formula | NMR Spectrum (δ value, p.p.m. TMS internal standard) |
|---|---|---|
| 3'-a | $C_{19}H_{21}NO_2$ | 1.15(3H, d, 7.5 Hz), 1.30–1.80 (4H, m), 1.9–2.55(3H, m), 6.12 (1H, t, 7.2 Hz), 7.0–7.7(7H, m), 8.35–8.65(2H, m), 8.90(1H) |
| 3'-b | $C_{19}H_{21}NO_2$ | 1.15(3H, d, 7.5 Hz), 1.30–1.80 (4H, m), 1.9–2.55(3H, m), 6.17 (1H, t, 7.2 Hz), 7.0–7.7(7H, m), 8.35–8.65(2H, m), 8.90(1H) |
| 3'-c | $C_{20}H_{23}NO_3$ | 0.90(3H, t, J = 7.2 Hz), 1.30–1.90 (6H), 2.00–2.50(3H), 6.12(1H, t, J = 7.2 Hz), 7.00–7.60(7H), 8.43(1H, dd, J = 4.8 and 1.5 Hz), 8.52(1H, d, J = 2.4 Hz), 8.53(1H) |
| 3'-d | $C_{25}H_{25}NO_2$ | 1.35–1.75(4H), 1.90–2.30(2H), 2.55–3.10(3H), 6.07(1H, t, J = 6.0 Hz), 7.00–7.55(12H), 8.50 (2H), 8.95(1H) |
| 3'-e | $C_{25}H_{25}NO_2$ | 1.40–1.70(4H), 1.90–2.30(2H), 2.55–3.20(3H), 6.10(1H, t, J = 6.0 Hz), 7.00–7.60(12H), 8.45– |

TABLE III-2-continued

| Compound | Formula melting point | NMR Spectrum (δ value, p.p.m. TMS internal standard) |
|---|---|---|
| 3'-f | $C_{21}H_{23}NO_2$ | 8.65(2H), 9.40(1H) 1.40–1.70(4H), 2.00–2.55(5H), 4.93(1H, d, J = 1 Hz), 5.10(1H, dd, J = 6 and 1 Hz), 5.76(1H), 6.11 (1H, t, J = 6.0 Hz), 7.00–7.55 (7H), 8.43(1H, dd, J = 4.8 and 1.5 Hz), 8.52(1H, d, J = 2.4 Hz), 8.80 (1H) |
| 3'-g | $C_{21}H_{23}NO_2$ | 1.40–1.70(4H), 2.00–2.55(5H), 4.93(1H, d, J = 1 Hz), 5.10(1H, dd, J = 6 and 1 Hz), 5.76(1H), 6.15 (1H, t, J = 6.0 Hz), 7.00–7.55 (7H), 8.43(2H), 8.52(1H) |
| 3'-h | $C_{21}H_{21}NO_2$ | 1.40–1.85(4H), 1.97(1H, t, J = 3 Hz), 2.10–2.35(2H), 2.35–2.65 (3H), 6.13(1H, t, J = 6.0 Hz), 7.00–7.50(7H), 8.43(1H), 8.52 (1H), 10.10(1H) |
| 3'-i | $C_{20}H_{23}NO_3$ | 1.40–1.70(4H), 2.20(2H), 2.65 (1H), 3.31(3H), 3.40–3.60(1H), 6.13(1H, t, J = 6.0 Hz), 7.00–7.55 (7H), 8.43(1H, dd, J = 4.8 and 1.5 Hz), 8.52(1H, d, J = 2.4 Hz), 8.60(1H) |
| 3'-j | $C_{19}H_{21}NO_2S$ | 1.35–1.75(4H), 1.80–2.60(5H), 4.93(1H), 5.10(1H), 5.50–6.10 (1H), 6.03(1H, t, J = 6.0 Hz, E), 6.20(1H, t, J = 6.0 Hz, Z), 6.46 (1H, Z), 6.75–7.70(4H, E; 3H, Z), 8.40–8.70(2H), 11.33 (1H) |
| 3'-k | $C_{23}H_{27}NO_2$ | 1.55–1.80(4H), 1.57(3H), 1.63 (3H), 2.00–2.50(5H), 5.10(1H, t, J = 6.0 Hz), 6.10(1H, t, J = 6.0 Hz), 7.00–7.60(7H), 8.45(1H, dd, J = 1.0 and 3.0 Hz), 8.52(1H, d, J = 1.0 Hz), 8.55(1H) |
| 3'-l | $C_{24}H_{27}NO_2$ | 0.9(3H), 1.30–1.80(6H), 1.90–2.70(7H), 6.13(1H), 7.00–7.60 (7H), 8.43(1H), 8.53(1H), 10.17(1H) |
| 3'-m | $C_{26}H_{31}NO_2$ | 0.83(3H), 1.10–1.90(10H), 1.95–2.70(7H), 6.13(1H), 7.00–7.55 (7H), 8.43(1H), 8.57(1H), 10.20(1H) |
| 3'-n | $C_{26}H_{24}N_2O_2$ | 1.55(4H, m), 2.10(2H, m), 2.85 (3H, m), 6.11(1H, t, 7 Hz), 7.30 (9H, m), 7.51(2H, d, 7 Hz), 8.39 (1H, dd, 2 Hz, 4 Hz), 8.60(1H, d, 2 Hz), 8.80(1H, COOH) |
| Compound | Formula melting point | NMR Spectrum (δ value, p.p.m. TMS internal standard) |
| 3'-o | $C_{18}H_{21}NO_2S$ | 1.20(6H, s), 1.46(6H, m), 2.36 (2H, m), 6.01(1H, t, 7 Hz), 6.84 (1H, d, 3 Hz), 7.00(1H, dd, 4 Hz, 3 Hz), 7.32(1H, d, 4 Hz), 7.55 (1H, dt, 2 Hz, 7 Hz), 8.46(1H, dd, 2 Hz, 4 Hz), 8.58(1H, d, 2 Hz), 9.05(1H, COOH) |
| 3'-p | $C_{18}H_{21}NO_2S$ 138–139° C. | 1.15(6H, s), 1.40(6H, m), 2.07 (2H, m), 6.20(1H, t, 7 Hz), 6.47 (1H, d, 3 Hz), 6.84(1H, dd, 4 Hz, 3 Hz), 7.10(1H, d, 4 Hz), 7.33 (1H, dd, 4 Hz, 7 Hz), 7.59(1H, dt, 2 Hz, 7 Hz), 7.49(1H, d, 2 Hz), 8.59(1H, dd, 2 Hz, 4 Hz), 9.70 (1H, COOH) |
| 3'-q | $C_{18}H_{21}NO_2S$ | 0.90(3H, t, J = 7.5 Hz), 1.35–1.85 (6H), 1.90–2.50(3H), 6.03(1H, t, J = 6.0 Hz, E), 6.20(1H, t, J = 6.0 Hz, Z), 6.46(1H, Z), 6.75–7.70(4H, E; 3H, Z), 8.45–8.70(2H), 10.20(1H) |

EXAMPLE 4

(Production Process 4)

Diisopropylamine (0.8 g, 8 mmole) was dissolved in tetrahydrofuran (10 ml) under argon, and the solution was cooled at −70° C., followed by adding dropwise 1.6M n-butyl lithium-hexane solution (5 ml) and stirring for 5 minutes. A solution of methyl (E)-7-phenyl-7-(3-pyridyl)-6-heptenoate (1.2 g, 4 mmole) in tetrahydrofuran (2 ml) was added dropwise to the reaction solution under the same conditions. 15 minutes later, a solution of phenyl disulfide (1 g, 5 mmole) in hexamethylphosphoramide (1 ml) was added dropwise under the same conditions. After the reaction was conducted for 30 minutes, 2N hydrochloric acid (5 ml) was added, and the reaction solution was restored to room temperature, followed by adjusting to pH 8 with aqueous sodium hydrogencarbonate. The product was extracted with ethyl acetate, and the organic layer was washed with water, dried and concentrated. The residue was chromatographed on silica gel, and development was effected with isopropyl ether:ethyl acetate (1:1) to yield methyl (E)-2-phenylthio-7-phenyl-7-(3-pyridyl)-6-heptenoate (4-e) (1.4 g, 85%).

The compounds (4-a through 4-i) as shown in Table IV were produced in accordance with the above procedure.

TABLE V

| Compound | $R^1$ | $R^2$ | $R^3$ | $R^4$ | $R^5$ | n | Isomer |
|---|---|---|---|---|---|---|---|
| 4-a | 3-Py | Ph | H | MeS | H | 3 | E |
| 4-b | 3-Py | Ph | H | PhS | H | 3 | E |
| 4-c | 3-Py | Ph | H | PhS | H | 3 | Z |
| 4-d | 3-Py | Ph | H | i-PrS | H | 3 | E |
| 4-e | 3-Py | Ph | Me | PhS | H | 3 | E |
| 4-f | 3-Py | Ph | Me | PhS | H | 3 | Z |
| 4-g | 3-Py | Ph | Me | i-PrS | H | 3 | E |
| 4-h | 3-Ph | Ph | Me | PhS | Me | 3 | E |
| 4-i | 3-Py | Ph | H | PhS | Me | 3 | E |

| Compound | Formula | NMR Spectrum (δ value, ppm, TMS internal standard) |
|---|---|---|
| 4-a | $C_{19}H_{21}NO_2S$ | 1.64(4H, m), 2.14(3H, s), 2.17 (2H, m), 3.17(1H, t, 7Hz), 6.14 (1H, t, 7Hz), 7.27(7H, m), 8.44(1H, dd, 2Hz, 4Hz), 8.64 (1H, d, 2Hz) |
| 4-b | $C_{24}H_{23}NO_2S$ | 1.75(4H, m), 2.17(2H, m), 3.65 (1H, t, 7Hz), 6.10(1H, t, 7Hz) 7.25(12H, m), 8.42(1H, dd, 2 Hz, 4Hz), 8.52(1H, d, 2Hz) |
| 4-c | $C_{24}H_{23}NO_2S$ | 1.73(4H, m), 2.07(2H, m), 3.62 (1H, t, 7Hz), 6.12(1H, t, 7Hz), 7.20(12H, m), 8.40(1H, m), 8.53 (1H, dd, 2Hz, 4Hz), 11.4(1H, COOH) |
| 4-d | $C_{22}H_{27}NO_2S$ | 0.91(3H, s), 0.99(3H, s), 1.69 (4H, m), 2.12(2H, m), 2.51(2H, m), 3.20(1H, m), 6.13(1H, t, 7 Hz), 7.30(7H, m), 8.50(2H, m), 10.40(1H, COOH) |
| 4-e | $C_{25}H_{25}NO_2S$ | 1.69(4H, m), 2.17(2H, m), 3.56 (1H, t, 7Hz), 3.61(3H, s), 6.03 (1H, t, 7Hz), 7.25(12H, m), 8.44(1H, dd, 2Hz, 4Hz), 8.50 (1H, d, 2Hz) |
| 4-f | $C_{25}H_{25}NO_2S$ | 1.69(4H, m), 2.11(2H, m), 3.57 (1H, t, 7Hz), 3.60(3H, s), 6.10 (1H, t, 7Hz), 7.18(12H, m), 8.41(1H, d, 2Hz), 8.52(1H, dd, 2Hz, 4Hz) |
| 4-g | $C_{23}H_{29}NO_2S$ | 0.98(6H, d, 8Hz), 1.68(4H, m), 2.20(2H, m), 2.43(2H, d, 7Hz), 3.15(1H, t, 8Hz), 3.71(3H, s), 6.06(1H, t, 7Hz), 7.33(7H, m), 8.42(1H, dd, 2Hz, 4Hz), 8.49 (1H, d, 2Hz) |
| 4-h | $C_{26}H_{27}NO_2S$ | 1.39(3H, s), 1.65(4H, m), 2.11 (2H, m), 3.63(3H, s), 6.05(1H, t, 7Hz), 7.30(12H, m), 8.43(2 H, m) |
| 4-i | $C_{25}H_{25}NO_2S$ | 1.41(3H, s), 1.70(4H, m), 2.10 (2H, m), 6.11(3H, t), 7.26(12 H,m), 8.48(2H,m) |

EXAMPLE 5

Procedure A (Production process 5):

Diisopropylamine (0.8 g, 8 mmole) was dissolved in tetrahydrofuran (10 ml) under argon, and the solution was cooled at −70° C., followed by adding dropwise 1.6M n-butyl lithium-hexane solution (5 ml) and stirring for 5 minutes. A tetrahydrofuran (2 ml) solution containing methyl 7-phenyl-7-(3-pyridyl)-6-heptenoate (1.19 g, 4 mmole) was added dropwise to the reaction solution. After stirring for 15 minutes under the same reaction conditions, acetone (0.5 ml) was added, and the reaction was carried out for another 10 minutes. Subsequently, 2N hydrochloric acid (5 ml) was added to terminate the reaction, and the temperature of the solution was allowed to rise to room temperature, followed by adding aqueous sodium hydrogencarbonate to adjust to pH 8. The product was extracted with ethyl acetate, and the organic layer was washed with water and dried. The residue was chromatographed on silica gel using isopropyl ether:ethyl acetate (1:1) to yield methyl (E)-2-(1-hydroxy-1-methylethyl)-7-phenyl-7-(3-pyridyl)-6-heptenoate (5-a) (1.2 g).

Procedure B (Production process 6):

Methyl (E)-2-(1-hydroxy-1-methylethyl)-7-phenyl-7-(3-pyridyl)-6-heptenoate (0.3 g, 0.89 mmole) was dissolved in dichloromethane (10 ml), and the solution was cooled at −10° C. Thionyl chlorde (0.15 ml) was added to the solution, followed by adding pyridine (0.4 ml) and stirring for 10 minutes under the same reaction conditions. After the completion of the reaction, aqueous sodium hydrogencarbonate (5 ml) was added, and the product was extracted with ethyl acetate. The organic layer was worked up in the usual procedure, and the crude product was chromatographed on silica gel, followed by elution with isopropyl ether:ethyl acetate (1:1) to yield methyl (E)-2-(1-methylethenyl)-7-phenyl-7-(3-pyridyl)-6-heptenoate (5-e) (0.25 g, 70%).

The compounds (5-a through 5-m) as shown in Table V were produced in accordance with the above Procedure A or B.

TABLE V

| Compound | $R^1$ | $R^2$ | $R^3$ | $R^4$ | $R^5$ | n | Isomer | Analogous Example |
|---|---|---|---|---|---|---|---|---|
| 5-a | 3-Py | Ph | Me | −C(Me)(Me)−OH | H | 3 | E | A |
| 5-b | 3-Py | Ph | Me | −C(Me)(Me)−OH | H | 3 | Z | A |
| 5-c | 3-Py | Ph | Me | cyclobutyl-OH | H | 3 | E | A |
| 5-d | 3-Py | Ph | Me | cyclobutyl | H | 3 | E | B |
| 5-e | 3-Py | Ph | Me | −C(Me)=CH₂ | H | 3 | E | B |

TABLE V-continued

| | | | | | | | | |
|---|---|---|---|---|---|---|---|---|
| 5-f | 3-Py | Ph | Me | Me−C(=CH$_2$) | H | 3 | Z | B |
| 5-g | 3-Py | Ph | H | Me−C(=CH$_2$) | H | 3 | E | B |
| 5-h | 3-Py | Ph | H | Me−C(=CH$_2$) | H | 3 | Z | B |
| 5-i | 3-Py | Ph | H | (cyclopentyl) | H | 3 | E | B |
| 5-j | 3-Py | Ph | H | Me−C(OH)−Me | H | 3 | E | A |
| 5-k | 3-Py | Ph | H | Me−C(OH)−Me | H | 3 | Z | A |
| 5-l | 3-Py | Ph | H | (cyclopentyl-OH) | H | 3 | E | A |
| 5-m | 3-Py | Ph | Me | (Ph)$_2$C−OH | H | 3 | E | A |

| Compound | Formula | NMR Spectrum (δ value, p.p.m. TMS internal standard) |
|---|---|---|
| 5-a | C$_{22}$H$_{27}$NO$_3$ | 1.20(6H, s), 1.51(4H, m), 2.24 (3H, m), 2.81(OH), 3.67(3H, s), 6.05(1H, t, 7 Hz), 7.32(7H, m), 8.41(1H, dd, 2 Hz, 4 Hz), 8.48 (1H, d, 2 Hz) |
| 5-b | C$_{22}$H$_{27}$NO$_3$ | 1.19(6H, s), 1.47(4H, m), 2.17 (2H, m), 2.34(1H, m), 2.70(OH), 3.67(3H, s), 6.11(1H, t, 7 Hz), 7.20(7H, m), 8.43(1H, d, 2 Hz), 8.54(1H, dd, 2 Hz, 4 Hz) |
| 5-c | C$_{24}$H$_{27}$NO$_3$ | 1.57(12H, m), 2.05(2H, m), 2.38 (1H, dd, 3 Hz, 9 Hz), 2.80(OH), 3.68(3H, s), 6.05(1H, t, 7 Hz), 7.31(7H, m), 8.41(1H, dd, 2 Hz, 4 Hz), 8.48(1H, d, 2 Hz) |
| 5-d | C$_{24}$H$_{25}$NO$_2$ | 1.66(6H, m), 2.23(6H, m), 3.13 (1H, m), 3.63(3H, s), 5.48(2H, m), 6.07(1H, t, 7 Hz), 7.29(7H, m), 8.43(1H, dd, 2 Hz, 4 Hz), 8.46(1H, d, 2 Hz) |
| 5-e | C$_{22}$H$_{25}$NO$_2$ | 1.47(4H, m), 1.70(3H, s), 2.11 (2H, m), 2.96(1H, t, 7 Hz), 3.63 (3H, s), 4.84(2H, m), 6.07(1H, t, 7 Hz), 7.30(7H, m), 8.41(1H, m), 8.50(1H, m) |
| 5-f | C$_{22}$H$_{25}$NO$_2$ | 1.48(4H, m), 1.70(3H, s), 2.14 (2H, m), 2.97(1H, t, 8 Hz), 3.61 (3H, s), 4.85(2H, m), 6.14(1H, t, 7 Hz), 7.20(6H, m), 7.46(1H, d, t, 2 Hz, 7 Hz), 8.44(1H, d, 2 Hz), 8.54(1H, dd, 2 Hz, 4 Hz) |
| 5-g | C$_{21}$H$_{23}$NO$_3$ | 1.49(4H, m), 1.76(3H, s), 2.21 (2H, m), 3.00(1H, t, 7 Hz), 4.87 (2H, m), 6.13(1H, t, 7 Hz), 7.29 (7H, m), 8.43(1H, dd, 2 Hz, 4 Hz), 8.56(1H, d, 2 Hz), 9.50 (1H, COOH) |
| 5-h | C$_{21}$H$_{23}$NO$_3$ | 1.50(4H, m), 1.76(3H, d, 2 Hz), 2.05(2H, m), 2.97(1H, t, 7 Hz), 4.84(2H, s), 6.14(1H, t, 7 Hz), 7.17(6H, m), 7.50(1H, dt, 2 Hz, 4 Hz), 8.42(1H, d, 2 Hz), 8.54 (1H, dd, 2 Hz, 4 Hz), 10.5 (1H, COOH) |
| 5-i | C$_{23}$H$_{25}$NO$_2$ | 1.60(6H, m), 2.29(6H, m), 3.13 (1H, t, 7 Hz), 5.51(1H, m), 6.12 (1H, t, 7 Hz), 7.29(7H, m), 8.43 (1H, dd, 2 Hz, 4 Hz), 8.53(1H, d, 2 Hz), 10.80(1H, COOH) |

| Compound | Formula melting point | NMR Spectrum (δ value, p.p.m. TMS internal standard) |
|---|---|---|
| 5-j | C$_{21}$H$_{25}$NO$_3$ | 1.19(3H, s), 1.27(3H, s), 1.57 (4H, m), 2.23(2H, m), 6.13(1H, t, 7 Hz), 7.31(7H, m), 8.41(1H, dd, 2 Hz, 4 Hz), 8.63(1H, d, 2 Hz) |
| 5-k | C$_{21}$H$_{25}$NO$_3$ | 1.20(3H, s), 1.27(3H, s), 1.61 (4H, m), 2.15(3H, m), 6.17(1H, t, 7 Hz), 7.19(7H, m), 7.65(2H, OH, COOH), 8.50(2H, m) |
| 5-l | C$_{23}$H$_{27}$NO$_3$ | 1.67(12H, m), 2.29(3H, m), 6.13 (1H, t, 7 Hz), 7.30(7H, m), 7.79 (2H, COOH, OH), 8.43(1H, m), 8.57(1H, m) |
| 5-m | C$_{32}$H$_{31}$NO$_3$ 113–114° C. | 1.37(4H, m), 2.00(2H, m), 3.50 (1H, m), 3.51(3H, s), 4.60(1H, s), 5.90(1H, t, 7 Hz), 7.29 (17H, m), 8.39(2H, m) |

EXAMPLE 6

(1) (Z)-2,2-dimethyl-7-(3-pyridyl)-7-(2-thienyl)-6-heptenoic acid (1.0 g) was heated in 50% aqueous phosphoric acid (20 ml) at 100° C. for 20 hours, and the product was separated and extracted in the conventional manner. High performance liquid chromatography of this crude product revealed that its E isomer/Z isomer ratio was E/Z=56:23. The crude product was separated in the same manner as Example 2 to give (E)-2,2-dimethyl-7-(3-pyridyl)-7-(2-thienyl)-6-heptenoic acid (0.48 g).

Nuclear magnetic resonance spectrum: 1.19(3H,s), 1.21(3H,s), 1.52(4H,m), 2.04(2H,m), 6.06(1H,t,7 Hz), 6.66(1H,m), 7.30(4H,m), 8.56(2H,m), 12.0(1H,COOH).

(2) (Z)-2,2-dimethyl-7-phenyl-7-(3-pyridyl)-6-heptenoic acid (0.1 g) was dissolved in 18% aqueous hydrochloric acid (1 ml) and the solution was heated at 100° C. for 21 hours. Extraction, separation and concentration in the conventional manner gave the crude product. High performance liquid chromatography of this crude product revealed that its E isomer/Z isomer ratio was E/Z=63:28. This crude product (85 mg) was subjected to preparative high performance chromatography to give (E)-2,2-dimethyl-7-phenyl-7-(3-pyridyl)-6-heptenoic acid (46 mg).

Nuclear magnetic resonance spectrum: 1.18(6H,s), 1.50(4H,m), 2.12(2H,m), 6.12(1H,t,7 Hz), 7.20(6H,m), 7.40(1H,dt,2 Hz,7 Hz), 8.44(1H,dd,2 Hz,4 Hz), 8.56(2H,d,2 Hz), 9.82(1H,COOH).

(3) (Z)-2,7-diphenyl-7-(3-pyridyl-6-heptenoic acid (200 mg) was dissolved in 50% aqueous phosphoric acid (2 ml) and the reaction was allowed to proceed with heating at 100° C. for 20 hours. After completion of the reaction, the product was extracted, washed and concentrated in the same manner. High performance liquid chromatography of an aliquot of the residue revealed that its E isomer/Z isomer ratio was 58:27. The E/Z mixture was subjected to preparative high performance liquid chromatography. The E isomer (120 mg) and Z isomer (61 mg) were thus independently obtained.

Examples of Pharmaceutical Composition

| (A) Capsule | |
| --- | --- |
| (1) Compound of 2-a | 50 mg |
| (2) Cellulose fine powder | 30 mg |
| (3) Lactose | 37 mg |
| (4) Magnesium stearate | 3 mg |
| Total | 120 mg |

All the metarials were mixed and filled into a gelatin capsule.

| (B) Soft Capsule | |
| --- | --- |
| (1) Compound of 2-c | 50 mg |
| (2) Corn starch oil | 100 mg |
| Total | 150 mg |

A mixed solution of (1) and (2) were prepared and filled into a soft capsule by a conventional manner.

| (C) Tablet | |
| --- | --- |
| (1) Compound of 2-a | 50 mg |
| (2) Lactose | 34 mg |
| (3) Corn starch | 10.6 mg |
| (4) Corn starch (gelatinized) | 5 mg |
| (5) Magnesium stearate | 0.4 mg |
| (6) Calcium Carboxymethyl cellulose | 20 mg |
| Total | 120 mg |

All the materials were mixed and compressed by a tabletting machine to prepare a tablet in accordance with a conventional manner.

EXPERIMENT 1

Inhibitory Action on Thromboxane $A_2$(TXA$_2$) Synthetase

As a specimen of TXA$_2$ synthetase was employed horse platelet microsomes treated with indomethacin (indomethacin-treated horse platelet microsomes: IPM), which were prepared according to the method described by Needleman et al. (Science 193 163, 1976).

to 60 $\mu$l of 50 mM tris-buffer solution (pH 7.5) of IPM (containing 140 $\mu$g as protein) was added 60 $\mu$l of the buffer solution or the solution containing the test compounds at various concentrations. The mixtures were left standing for 5 minutes at room temperature. Then at 0° C. to 100 $\mu$l portion of the mixture was added 20 $\mu$l of the buffer solution containing 30 ng of prostaglandin H$_2$(PGH$_2$). The mixtures were left standing for 5 minutes at 0° C. to cause formation of thromboxane A$_2$(TXA$_2$). The reaction of thromboxane A$_2$ production was stopped by the addition of 500 $\mu$l of the tris-buffer to the mixture. Using 50 $\mu$l of the mixtures, the quantitative determination of thromboxane B$_2$(TXB$_2$), a stable metabolite of TXA$_2$, was done by means of the radioimmunoassay (Shibouta et al., Biochem. Pharmacol. 28 3601, 1979).

The inhibitory activity of the compounds on TXA$_2$-synthetase was determined from the difference in the production of TXB$_2$ between the test group and the control group.

The results on typical compounds are shown by Table VI below:

TABLE VI

| Compound | % Inhibition on thromboxane A$_2$ synthetase | |
| --- | --- | --- |
| | $3 \times 10^{-8}$ M | $10^{-7}$ M |
| 1-b | 45 | 80 |
| 1-d | 57 | 85 |
| 1-e | 45 | 80 |
| 1-l | 48 | 90 |
| 1-m | 44 | 92 |
| 2-a | 83 | 92 |
| 2-b | 49 | 90 |
| 2-c | 92 | 97 |
| 2-d | 62 | 92 |
| 2-e | 65 | 90 |
| 2-n | 41 | 96 |
| 3'-e | 33 | 90 |
| 3'-h | 66 | 93 |
| 3'-i | 42 | 88 |
| 3'-n | 57 | 93 |
| 3'-o | 60 | 92 |
| 3'-p | 46 | 90 |
| 4-a | 52 | 84 |
| 4-b | 60 | 93 |
| 4-c | 50 | 88 |
| 4-h | 30 | 87 |
| 5-g | 59 | 92 |
| 5-i | 32 | 77 |
| 5-j | 41 | 81 |

What is claimed is:

1. A compound of the formula:

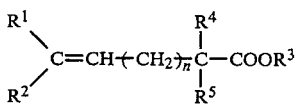

wherein $R^1$ is a pyridyl group; $R^2$ is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; $R^3$ is hydrogen, benzyl or a lower alkyl; one of $R^4$ and $R^5$ is hydrogen or a lower alkyl, and the other is an aryloxy, or a lower aliphatic hydrocarbon, an alicyclic hydrocarbon having not more than 6 carbon atoms or an aromatic group which may have a substituent, or a group represented by the formula, $—S(O)_m—R^6$ (in which $R^6$ is phenyl or a lower alkyl group; m is an integer of 0 to 2), or $R^4$ and $R^5$ each combine with the other to represent one alkylene group; and n is an integer of 2 to 6, or a pharmaceutically acceptable salt thereof.

2. A compound as claimed in claim 1, wherein $R^1$ is 3-pyridyl.

3. A compound as claimed in claim 1, wherein $R^2$ is phenyl.

4. A compound as claimed in claim 1, wherein $R^2$ is 2-thienyl.

5. A compound as claimed in claim 1, wherein n is 3 or 4.

6. A compound as claimed in claim 1, wherein one of $R^4$ and $R^5$ is hydrogen or methyl.

7. A compound as claimed in claim 1, wherein one of $R^4$ and $R^5$ is hydrogen and the other is methyl.

8. A compound as claimed in claim 1, wherein $R^4$ is methyl and $R^5$ is methyl.

9. A compound as claimed in claim 1, wherein $R^3$ is hydrogen.

10. A compound as claimed in claim 1, wherein $R^3$ is a lower alkyl group.

11. A compound as claimed in claim 1, wherein the compound is 2,2-dimethyl-7-phenyl-7-(3-pyridyl)-6-heptenoic acid.

12. A compound as claimed in claim 1, wherein the compound is 2,2-dimethyl-7-(3-pyridyl)-7-(2-thienyl)-6-heptenoic acid.

13. A pharmaceutical composition suitable for inhibiting activity of thromboxane A₂ synthetase in a mammal, which comprises, as an active ingredient, an effective amount of a compound of the formula:

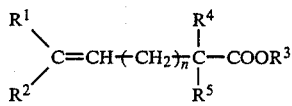

wherein R¹ is a pyridyl group; R² is a phenyl, thienyl, furyl, naphthyl, benzothienyl or pyridyl group which may have as a substituent a lower alkoxy, a lower alkyl, a halogen, trifluoromethyl, a lower alkenyl or methylenediozy; R³ is hydrogen, benzyl or a lower alkyl; one of R⁴ and R⁵ is hydrogen or a lower alkyl, and the other is an aryloxy, or a lower aliphatic hydrocarbon, an alicyclic hydrocarbon having not more than 6 carbon atoms or an aromatic group which may have a substituent, or a group represented by the formula, —S(O)ₘ—R⁶ (in which R⁶ is phenyl or a lower alkyl group; m is an integer of 0 to 2), or R⁴ and R⁵ each combine with the other to represent one alkylene group; and n is an integer of 2 to 6, or a pharmaceutically acceptable salt thereof, and a pharmaceutical acceptable carrier or excipient therefor.

14. A method for producing a compound of the formula:

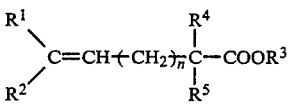

wherein R¹ is a pyridyl group; R² is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; R³ is hydrogen, benzyl or a lower alkyl; one of R⁴ and R⁵ is hydrogen or a lower alkyl, and the other is an aryloxy, or a lower aliphatic hydrocarbon, an alicyclic hydrocarbon having not more than 6 carbon atoms or an aromatic group which may have a substituent, or a group represented by the formula, —S(O)ₘ—R⁶ (in which R⁶ is phenyl or a lower alkyl group; m is an integer of 0 to 2), or R⁴ and R⁵ each combine with the other to represent one alkylene group; n is an integer of 2 to 6, which comprises reacting a compound of the formula:

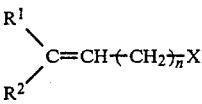

(wherein R¹, R² and n are as defined above, and X is a halogen atom) with a compound of the formula:

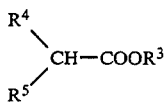

(wherein R³, R⁴ and R⁵ are as defined above).

15. A method for producing a compound of the formula:

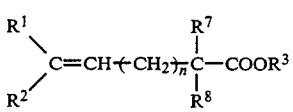

(wherein R¹ is a pyridyl group; R² is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; R³ is hydrogen, benzyl or a lower alkyl; one of R⁷ and R⁸ is a hydrogen atom or a lower alkyl group, and the other is a lower aliphatic hydrocarbon group and n is an integer of 2 to 6), which comprises reacting a compound of the formula:

(wherein R¹ and R² are as defined above) with a compound of the formula:

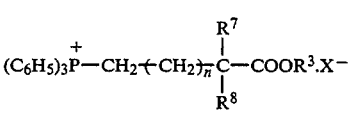

wherein R³, R⁷, R⁸, and n are as defined above, and X⁻ is a halogen ion.

16. A method for producing a compound of the formula:

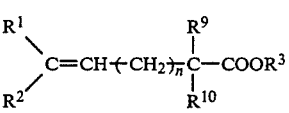

(wherein R¹ is a pyridyl group; R² is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; R³ is hydrogen, benzyl or a lower alkyl; R⁹ is hydrogen or a lower alkyl or arylthio; R¹⁰ is a lower aliphatic hydrocarbon group; and n is as defined above), which comprises reacting a compound of the formula:

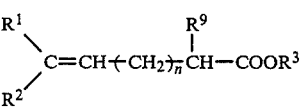

(wherein R¹, R², R³, R⁹ and n are as defined above) with a compound of the formula:

(wherein X is a halogen; and $R^{10}$ is as defined above).

17. A method for producing a compound of the formula:

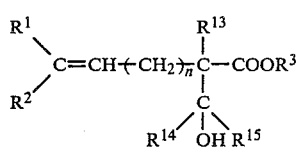

(wherein $R^1$ is a pyridyl group; $R^2$ is a phenyl, thienyl, furyl, naphthyl, benzothienyl or pyridyl group which may have as a substituent a lower alkoxy, a lower alkyl, a halogen, trifluoromethyl, a lower alkenyl or methylenedioxy; $R^3$ is hydrogen, benzyl or a lower alkyl; $R^{13}$ is a hydrogen atom or a lower alkyl group; $R^{14}$ and $R^{15}$ each represent a lower alkyl or an aryl group, or combine with the other to represent one alkylene group; and n is an integer of 2 to 6), which comprises reacting a compound of the formula:

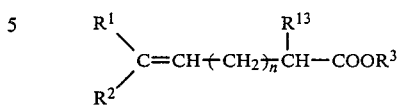

(wherein $R^1$, $R^2$, $R^3$, $R^{13}$ and n are as defined above) with a compound of the formula:

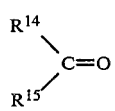

(wherein $R^{14}$ and $R^{15}$ are as defined above).

* * * * *